US 9,527,916 B2

(12) United States Patent
Van Eenennaam et al.

(10) Patent No.: US 9,527,916 B2
(45) Date of Patent: Dec. 27, 2016

(54) AGONISTIC ANTIBODY TO CD27

(71) Applicant: ADURO BIOTECH HOLDINGS, EUROPE B.V., Oss (NL)

(72) Inventors: Hans Van Eenennaam, Oss (NL); Winfried Robert Mulder, Oss (NL); Jannetje Geertruida Borst, Amsterdam (NL); Aartje Maria Elizabeth Veraar, Oss (NL); Paul Maria Frederikus Vink, Oss (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 722 days.

(21) Appl. No.: 13/719,723

(22) Filed: Dec. 19, 2012

(65) Prior Publication Data
US 2013/0183316 A1 Jul. 18, 2013

Related U.S. Application Data

(63) Continuation-in-part of application No. PCT/EP2011/061557, filed on Jul. 7, 2011.

(30) Foreign Application Priority Data

Jul. 9, 2010 (EP) ..................................... 10169021

(51) Int. Cl.
*A61K 39/395* (2006.01)
*C07K 16/28* (2006.01)
*A61K 45/06* (2006.01)

(52) U.S. Cl.
CPC ....... *C07K 16/2878* (2013.01); *A61K 39/3955* (2013.01); *A61K 45/06* (2013.01); *C07K 2317/75* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,229,289 A | 7/1993 | Kjeldsen et al. | |
| 8,481,029 B2 | 7/2013 | Glennie et al. | |
| 2003/0035790 A1 | 2/2003 | Chen et al. | |
| 2003/0091995 A1* | 5/2003 | Buechler ............ | A01K 67/0275 435/6.14 |
| 2008/0171014 A1* | 7/2008 | Wu ........................ | C07K 14/47 424/85.2 |
| 2010/0173324 A1 | 7/2010 | Mori et al. | |
| 2011/0033449 A1 | 2/2011 | Glennie et al. | |
| 2011/0274685 A1* | 11/2011 | Keler ................. | C07K 16/2878 424/133.1 |
| 2013/0336976 A1 | 12/2013 | Glennie et al. | |

FOREIGN PATENT DOCUMENTS

| | | |
|---|---|---|
| EP | 2 314 628 | 4/2011 |
| JP | 2010-506925 | 3/2010 |
| WO | 2004/060319 | 7/2004 |
| WO | WO 2008/051424 | 5/2008 |

OTHER PUBLICATIONS

Damschroder et al. (Mol Immunol. Aug. 2004;41(10):985-1000).*
Wesolowski et al, Med Microbiol Immunol (2009) 198:157-174.*
Penichet et al., Drug Development Research 61:121-136 (2004).*
Vajdos et al. (J Mol Biol. Jul. 5, 2002;320(2):415-28).*
Rudikoff et al. (Proc. Natl. Acad. Sci. USA, 79: 1979-1983, Mar. 1982).*
Brown et al. (J Immunol. May 1, 1996;156(9):3285-91).*
Japanese Office Action dated Aug. 4, 2015, which issued during prosecution of Japanese Application No. 2013-517396.
He, et al. "Abstract 5343: Development of novel anti-CD27 human antibodies with therapeutic potential" Cancer Research 70:5343, Apr. 15, 2010.
French, Ruth R., et al., "Eradication of lymphoma by CD8 T cells following anti-CD40 monoclonal antibody therapy is critically dependent on CD27 costimulation," Blood 2007, 109: 4810-4815.
He, Lizhen, et al., "Development of Novel Anti-CD27 Human Antibodies with Therapeutic Potential," Celldex Therapeutics Inc., XP009140790, Apr. 21, 2010.
Sakanishi, Tamami, et al., "Anti-tumor effects of depleting and non-depleting anti-CD27 monoclonal antibodies in immune-competent mice," Biochemical and Biophysical Research Communications 393 (2010) 829-835.
International Search Report corresponding to PCT/EP2011/061557 mailed Nov. 22, 2011.
Xu, et al. "FcγRs Modulate Cytotoxicity of Anti-Fas Antibodies: Implications for Agonistic Antibody-Based Therapeutics" The Journal of Immunology, Jul. 2003, 171(2):562-568.
Zou. "Regulatory T cells, tumour immunity and immunotherapy" Nature Reviews Immunology, Apr. 2006, 6(4):295-307.
Giuntoli II, et al. "Direct Costimulation of Tumor-reactive CTL by Helper T Cells Potentiate Their Proliferation, Survival, and Effector Function" Clinical Cancer Research, Mar. 2002, 8:922-931.
Watts. "TNF/TNFR Family Members in Costimulation of T Cell Responses" Annu. Rev. Immunol., 2005, 23:23-68.

(Continued)

*Primary Examiner* — Zachary Skelding
(74) *Attorney, Agent, or Firm* — Vedder Price P.C.; Thomas J. Kowalski; Deborah L. Lu

(57) ABSTRACT

The invention relates to a binding compound, which binds the same epitope of human CD27 as monoclonal antibody hCD27.15, produced by hybridoma hCD27.15 which was deposited with the ATCC in on Jun. 2, 2010 under number PTA-11008. In particular the invention relates to such a binding compound of claim 1 which may comprise: an antibody heavy chain variable region which may comprise at least one CDR selected from the group consisting of SEQ ID NOs: 5, 6 and 7, or a variant of any of said sequences; and/or an antibody light chain variable region which may comprise at least one CDR selected from the group consisting of SEQ ID NOs: 8, 9 and 10, or a variant of any of said sequences.

19 Claims, 6 Drawing Sheets

(56) References Cited

OTHER PUBLICATIONS

Goodwin, et al. "Molecular and Biological Characterization of a Ligand for CD27 Defines a New Family of Cytokines with Homology to Tumor Necrosis Factor" Cell, May 1993, 73:447-456.
Rowley, et al. "Stimulation by Soluble CD70 Promotes Strong Primary and Secondary CD8+ Cytotoxic T Cell Responses In Vivo" The Journal of Immunology, May 2004, 172(10):6039-6046.
Abbas, et al. "Functional diversity of helper T lymphocytes" Nature, Oct. 1996, 383:787-793.
Adams, et al. "Monoclonal antibody therapy of cancer" Nature Biotechnology, Sep. 2005, 23(9):1147-1157.
Alegre, et al. "An anti-murine CD3 monoclonal antibody with a low affinity for Fcγ receptors suppresses transplantation responses while minimizing acute toxicity and immunogenicity" The Journal of Immunology, Aug. 1995,155(3):1544-1555.
Arens, et al. "Constitutive CD27/CD70 Interaction Induces Expansion of Effector-Type T Cells and Results in IFNγ-Mediated B Cell Depletion" Immunity, Nov. 2001, 15:801-812.
Arens, et al. "Tumor Rejection Induced by CD70-mediated Quantitative and Qualitative Effects on Effector CD8+ T Cell Formation" The Journal of Experimental Medicine, Jun. 2004, 199(11):1595-1605.
Banner, et al. "Crystal structure of the soluble human 55 kd TNF receptor-human TNFβ complex: implications for TNF receptor activation" Cell, May 1993, 73(3):431-445.
Bigler, et al. "Definition of three epitopes of the CD27 molecule [P 120->55] present on activated normal lymphocytes" T-Cell Antigens-Papers, Leukocyte Typing IV, 1989, 351-352.
Booy, et al. "Monoclonal and bispecific antibodies as novel therapeutics" Arch. Immunol. Ther. Exp., 2006, 54:85-101.
Camerini, et al. "The T cell activation antigen CD27 is a member of the nerve growth factor/tumor necrosis factor receptor gene family" The Journal of Immunology, Nov. 1991, 147(9):3165-3169.
Cormary, et al. "Induction of T-cell antitumor immunity and protection against tumor growth by secretion of soluble human CD70 molecules" Cancer Gene Therapy, 2004, 11:497-507.
Couderc, et al. "Enhancement of antitumor immunity by expression of CD70 (CD27 ligand) or CD154 (CD40 ligand) costimulatory molecules in tumor cells" Cancer Gene Therapy, 1998, 5(3):163-175.
Cragg, et al. "Signaling antibodies in cancer therapy" Current Opinion in Immunology, Oct. 1999, 11(5):541-547.
Croft. "Co-Stimulatory Members of the TNFR Family: Keys to Effective T-Cell Immunity?" Nature Reviews Immunology, Aug. 2003, 3(8):609-620.
Dong, et al. "CD148 and CD27 are Expressed in B Cell Lymphomas Derived from both Memory and Naive B Cells" Leukemia and Lymphoma, 2002, 43(9):1855-1858.
Engelmann, et al. "Antibodies to a soluble form of a tumor necrosis factor (TNF) receptor have TNF-like activity" The Journal of Biological Chemistry, Aug. 1990, 265(24):14497-14504.
French, et al. "CD40 antibody evokes a cytotoxic T-cell response that eradicates lymphoma and bypasses T-cell help" Nature Medicine, May 1999, 5(5):548-553.
Glennie, et al. "Clinical trials of antibody therapy" Immunology Today, Aug. 2000, 21(8):403-410.
Gravestein, et al. "Novel mAbs reveal potent co-stimulatory activity of murine CD27" International Immunology, Apr. 1995, 7(4):551-557.
Gravestein, et al. "CD27 Cooperates with the Pre-T Cell Receptor in the Regulation of Murine T Cell Development" The Journal of Experimental Medicine, Aug. 1996, 184(2):675-685.
Gravestein, et al. "The TNF receptor family member CD27 signals to Jun N-terminal kinase via Traf-2" European Journal of Immunology, Jul. 1998, 28(7):2208-2216.
Gray, et al. "Therapeutic potential of immunostimulatory monoclonal antibodies" Clinical Science, Jul. 2006, 111(2):93-106.

Gruss, et al. "Tumor necrosis factor ligand superfamily: involvement in the pathology of malignant lymphomas" Blood, Jun. 1995, 85(12):3378-3404.
Haswell, et al. "Analysis of the oligomeric requirement for signaling by CD40 using soluble multimeric forms of its ligand, CD154" European Journal of Immunology, Oct. 2001, 31(10):3094-3100.
Hendriks, et al. "CD27 is required for generation and long-term maintenance of T cell immunity" Nature Immunology, Nov. 2000, 1(5):433-440.
Hendriks, et al. "CD27 Promotes Survival of Activated T Cells and Complements CD28 in Generation and Establishment of the Effector T Cell Pool" The Journal of Experimental Medicine, Nov. 2003, 198(9):1369-1380.
Hendriks. "Contributions of CD27 and relatives to the specific immune response" PhD Thesis, Chapter 2, 2004.
Hurwitz, et al. "Costimulatory wars: the tumor menace" Current Opinion in Immunology, 2000, 12:589-596.
Jokiranta, et al. "Biotinylation of Monoclonal Antibodies Prevents Their Ability to Activate the Classical Pathway of Complement" The Journal of Immunology, Aug. 1993, 151(4):2124-2131.
Kedl, et al. "CD40 stimulation accelerates deletion of tumor-specific CD8+ T cells in the absence of tumor-antigen vaccination" PNAS, Sep. 2001, 98(19):10811-10816.
Kelly, et al. "Induction of tumor-specific T cell memory by NK cell-mediated tumor rejection" Nature Immunology, Jan. 2002, 3(1):83-90.
Kobata, et al. "CD27 is a signal-transducing molecule involved in CD45RA+ naive T cell costimulation" The Journal of Immunology, 1994, 153:5422-5432.
Leach, et al. "Enhancement of Antitumor Immunity by CTLA-4 Blockade" Science, Mar. 1996, 271:1734-1736.
Lorenz, et al. "Anti-Tumor Immunity Elicited by a Recombinant Vaccinia Virus Expressing CD70 (CD27L)" Human Gene Therapy, May 1999, 10:1095-1103.
Matter, et al. "Elimination of chronic viral infection by blocking CD27 signaling" The Journal of Experimental Medicine, Aug. 2006, 203(9):2145-2155.
Nieland, et al. "CD40 and CD70 Co-Stimulate a Potent In Vivo Antitumor T Cell Response" Journal of Immunotherapy, 1998, 21(3):225-236.
Nolte, et al. "The price of the CD27-CD70 costimulatory axis: you can't have it all" The Journal of Experimental Medicine, Oct. 2006, 203(11):2405-2408.
Pardoll. "Spinning Molecular Immunology into Successful Immunotherapy" Nature Reviews Immunology, Apr. 2002, 2:227-238.
Park, et al. "Monoclonal Antibody Therapy" Advances in Protein Chemistry, 2001, 56:369-421.
Parlevliet, et al. "In Vivo Effects of IgA and IgG2a Anti-CD3 Isotype Switch Variants" Journal of Clinical Investigation, Jun. 1994, 93(6):2519-2525.
Raju. "Glycosylation Variations with Expression Systems and Their Impact on Biological Activity of Therapeutic Immunoglobulins" BioProcess International, Apr. 2003, pp. 44-53.
Roberts, et al. "Control of established melanoma by CD27 stimulation is associated with enhanced effector function and persistence, and reduced PD-1 expression, of tumor infiltrating CD8+ T cells" Journal of Immunotherapy, Oct. 2010, 33(8):769-779.
Santa Cruz Biotechnology. "CD27 (M-T271): sc-19653".
Schwabe, et al. "Modulation of Soluble CD40 Ligand Bioactivity with Anti-CD40 Antibodies" Hybridoma, 1997, 16(3):217-225.
Takeda, et al. "CD27-Mediated Activation of Murine NK Cells" The Journal of Immunology, 2000, 164:1741-1745.
Tao, et al. "Role of Carbohydrate in the Structure and Effector Functions Mediated by the Human IgG Constant Region" The Journal of Immunology, Oct. 1989, 143(8):2595-2601.
Taraban, et al. "Cutting Edge: A Critical Role for CD70 in CD8 T Cell Priming by CD40-Licensed APCs" The Journal of Immunology, 2004, 173:6542-6546.
Tutt, et al. "T Cell Immunity to Lymphoma Following Treatment with Anti-CD40 Monoclonal Antibody" The Journal of Immunology, 2002, 168:2720-2728.

(56) References Cited

OTHER PUBLICATIONS

Van Lier, et al. "Tissue Distribution and Biochemical and Functional Properties of Tp55 (CD27), A Novel T Cell Differentiation Antigen" The Journal of Immunology, Sep. 1987, 139(5):1589-1596.

van Mierlo, et al. "CD40 stimulation leads to effective therapy of CD40-tumors through induction of strong systemic cytotoxic T lymphocyte immunity" PNAS, Apr. 2002, 99(8):5561-5566.

Wieland, et al. "CD27 contributes to the early systemic immune response to Mycobacterium tuberculosis infection but does not affect outcome" International Immunology, Sep. 2006, 18(11):1531-1539.

* cited by examiner

Fig. 6

A hCD27.15 Heavy Chain amino acid sequence

```
<----------FWR1----------> <--CDR1--> <----FWR2---->
EVRLQQSGADLVKPGASVKLSCTAS  GFIIKATYMH WVRQRPEQGLEWIG

<------CDR2-----> <-------------FWR3------------->
RIDPANGETKYDPKFQV KATITADTSSSTAYLQLNSLTSDDTAVYYCAR

<CDR3-> <----------FWR4---------->
YAWYFDV WGAGTTVTVSSAKTTPPXVYPXXPGS
```

B hCD27.15 Light Chain amino acid sequence

```
<--------FWR1----------> <--CDR1---> <---FWR2------>
DIQMTQSPASLSASVGDTVTITC  RASENIYSFLA WYHQKQGRSPQLLVY

<CDR2-> <--------------FWR3-------------->
HAKTLAE GVPSRFSGSGSGTQFSLKINSLQAEDFGSYYC

<-CDR3--> <-------------FWR4------------>
QHYYGSPLT FGAGTKLEVKRADAAPTVSIFPPSSEELSL
```

AGONISTIC ANTIBODY TO CD27

RELATED APPLICATIONS AND INCORPORATION BY REFERENCE

This application is a continuation-in-part application of international patent application Serial No. PCT/EP2011/061557 filed 7 Jul. 2011, which published as PCT Publication No. WO 2012/004367 on 12 Jan. 2012, which claims benefit of European patent application Serial No. 10169021.2 filed 9 Jul. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to an isolated antibody or fragments thereof which bind to human CD27, polynucleotides encoding such antibody and host cells producing said antibody. The antibody may be used to stimulate lymphocyte proliferation and/or survival, to treat cancer and to combat autoimmunity or transplant rejection. In addition, the antibody may be used as a diagnostic tool and in vitro agent to promote proliferation and/or survival of $CD27^+$ cells.

BACKGROUND OF THE INVENTION

CD27, a TNF receptor family member was identified as a membrane molecule on human T cells (van Lier et al., 1987, *J Immunol* 139:1589-96). According to current evidence, CD27 has a single ligand, CD70, which is also a TNF family member (Goodwin et al., 1993, *Cell* 73:447-56). CD27 and CD70 have also been identified and cloned in the mouse system (Gravestein et al., 1993, *Eur J Immunol* 23:943-50; Tesselaar et al., *J Immunol* 159:4959-65).

CD27 is exclusively expressed by hematopoietic cells, in particular those of the lymphocyte lineage, i.e. T-, B- and NK cells. In the human system, CD27 expression in the $\alpha\beta$ T cell lineage is induced during positive selection of thymocytes and maintained in naive conventional $CD4^+$ and $CD8^+$ T cells (Vanhecke et al., 1997, *J Immunol* 159:5973-83). Upon T cell activation via the T cell antigen receptor (TCR), CD27 expression increases, in a transient manner (van Lier et al., 1987, *J Immunol* 139:1589-96). Next, CD27 is shed from the surface of activated T cells and the soluble form of CD27 can be detected in the serum marker for (chronic) T cell activation (Hintzen et al., 1991, *J Immunol* 147:29-35). Among peripheral T cells, permanent loss of CD27 expression results from persistent antigenic stimulation and hallmarks terminally differentiated effector/memory T cells, while central memory T cells maintain CD27 (Baars et al., 1995, *J Immunol* 154:17-25; Hamann et al., 1997, *J Exp Med* 186:1407-18). CD27 is also expressed on human $\gamma\delta$ T cells and induced during thymic development (Offner F et al, 1997, *J Immunol* 158:4634-41). Moreover, loss of CD27 expression is a hallmark of chronically stimulated $\gamma\delta$ T cells (Gioia C et al., 2002, *J Immunol* 168:1484-9). Generally, CD27 is an exquisite marker for cellular activation and differentiation stages and used as such in human clinical diagnostics and research.

In the mouse, CD27 was found on hematopoietic stem cells, multipotent progenitors and common lymphoid precursors (Medina et al., 2001, *Nat Immunol* 2:718-24; Wiesmann et al., 2000, *Immunity* 12:193-9).

CD27 was originally defined as a human T-cell co-stimulatory molecule that increments the proliferative response to TCR stimulation (van Lier et al., 1987, *J Immunol* 139:1589-96). Presence of CD70 dictates the timing and persistence of CD27-mediated co-stimulation. Upon immune activation, dendritic cells, T-, B- and NK cells transiently express CD70, contingent upon the presence of antigen, Toll-like receptor agonists or inflammatory cytokines.

CD27 stimulation using anti-CD27 mAb CLB-CD27/1 (9F4) incremented the proliferative response of human T cells to TCR stimulation (Van Lier et al., 1987, *J Immunol* 139:1589-96). This was confirmed using crosslinked anti-CD27 mAb 1A4, or transfectants expressing CD70. Conversely, antibodies directed to CD27 or CD70 could block this proliferation. Both $CD4^+$ and $CD8^+$ T cells responded to CD27 co-stimulation (Goodwin et al., 1993, *Cell* 73:447-56; Kobata et al., 1994, *J Immunol* 153:5422-32; Hintzen et al., 1995, *J Immunol* 154:2612-23). Studies in mice unambiguously support the role of CD27 as a co-stimulatory receptor for naive $CD8^+$ and $CD4^+$ $\alpha\beta$ T cells. For mouse T cells, CD27 primarily promotes their survival upon TCR-mediated activation, but in human T cells, it additionally promotes cell cycle entry and/or activity (reviewed in Borst et al., 2005, *Curr Op Immunol* 17:275-281; Nolte et al., 2009, *Immunol Rev* 229:216-231).

Upon its transient engagement as occurs in acute infections that temporarily upregulate CD70, CD27 supports the generation of a $CD8^+$ effector T cell pool in priming organs, its maintenance at the tissue effector site, its conversion into memory cells and its potential to exercise memory function (Hendriks et al., 2003, *J Exp Med* 198:1369-1380; Hendriks et al. 2005, *J Immunol* 175:1666-75, Xiao et al, 2008, *J Immunol* 181:1071-82). Studies with CD70 blocking antibody in mouse models support the concept that CD27-CD70 interactions can make an important contribution to generation of $CD8^+$ effector T cells, e.g. after protein immunization, virus infection and allotransplantation (Taraban et al., 2004, *J Immunol* 173:6542-46; Bullock and Yagita, 2005, *J Immunol* 174:710-17; Yamada et al., 2005, *J Immunol* 174:1357-1364; Schildknecht et al., 2007, *Eur J Immunol* 37:716-28).

Transgenic expression of CD70 in immature dendritic cells sufficed to convert immunological tolerance to virus or tumors into $CD8^+$ T cell responsiveness upon immunization with MHC class I-restricted peptide in PBS. Likewise, agonistic soluble CD70 promoted the $CD8^+$ T cell response upon such peptide immunization (Rowley et al., 2004, *J Immunol* 172:6039-6046) and in CD70 transgenic mice, $CD^+$ and $CD8^+$ effector cell formation in response to TCR stimulation was greatly facilitated (Arens et al. 2001, *Immunity* 15:801-12; Tesselaar et al., 2003, *Nat Immunol* 4:49-54; Keller et al. 2008, *Immunity* 29:334-346). In mouse lymphoma models, tumor rejection was improved upon CD70 transgenesis or injection of an activating anti-mouse CD27 antibody (Arens et al., 2003, *J Exp Med* 199:1595-1605;

French et al., 2007, *Blood* 109:4810-15; Sakanishi and Yagita, 2010, *Biochem. Biophys. Res. Comm.* 393:829-835; WO 2008/051424).

Generally, CD27 expression on lymphoid cells is associated with survival potential. Salient examples come from human adoptive T cell therapies, in cancer and AIDS patients, where long-term persisting T cells were selected for CD27 expression. In addition, CD70 expression on tumor-infiltrating lymphocytes was positively correlated with an anti-tumor immune response, potentially reflecting effector T cell survival within the tumor (Ochsenbein et al., 2004, *J Exp Med* 200:1407-17; Huang et al., 2006, *J Immunol* 176:7726-35).

For conventional $CD^+$ T cells, CD27 similarly promotes primary and secondary responses (Hendriks et al., 2000, *Nat Immunol* 1:433-40; Xiao et al, 2008, *J Immunol* 181:1071-82). Moreover, CD27 co-stimulation favours an IL-12 independent pathway for T helper-1 development and enables $CD^+$ T cells to provide help for memory programming of $CD8^+$ T cells (Soares et al., 2007, *J Exp Med* 204:1095-106; Xiao et al, 2008, *J Immunol* 181:1071-8). In C57BL/6 mice, CD27 stimulation is consistently associated with Th1-type $CD^+$ T cell differentiation (Arens et al. 2001, *Immunity* 15:801-12; Soares et al., 2007, *J Exp Med* 204:1095-106; Xiao et al, 2008, *J Immunol* 181:1071-82) and in human $CD^+$ T cells in vitro, CD27 promoted Th1 development in presence of IL-12, but had no differentiation-inducing effect in presence of IL-4 (van Oosterwijk et al., 2007, *Int Immunol* 19:713-18).

In addition, CD27 stimulation was demonstrated to promote human regulatory T cell generation and/or function (Jacquot et al., 1997, *Cell Immunol* 179:48-54). Amongst natural regulatory T cells in human, high CD27 expression hallmarks the cells that have the highest suppressive activity and the CD27 high subpopulation is preferentially amplified during rapamycin treatment (Koenen et al., 2005, *J Immunol* 174:7573-83; Coenen et al., 2006, *Blood* 107:1018-23). Recent observations suggest that the $CD27^+$ Treg subpopulation can differentiate into Th17 cells (Koenen et al., 2008, *Blood* 112:2340-52). Interestingly, $CD70^+$ B lymphoma cells were found to stimulate Treg formation and impede Th17 differentiation by CD27 triggering on intratumoral T cells (Yang et al., 2007, *Blood* 110:2537-44; Yang et al., 2009, *Cancer Res* 69:5522-30).

In resting B cells, CD27 expression 1s absent, but it is induced during B cell activation in germinal centers and in human, it is subsequently maintained on memory B cells and plasma cells (Agematsu et al., 2000 *Immunol Today* 21:204-206; Jung et al., 2000, *Eur J Immunol* 30:2437-2443). CD27 also acts as a co-stimulatory receptor on B cells. In in vitro systems with human B cells, CD27-CD70 interactions consistently stimulate Ig secretion (Agematsu et al., 1997, *Eur J Immunol* 27:2073-79; Jacquot et al., 1997, *J Immunol* 159:2652-7).

Human NK cells can be subdivided into two functional subsets based on CD27 expression with lack of CD27 expression identifying the mature effector cells (Sugita et al., 1992, *J Immunol* 149:1199-203; Vossen et al., 2008, *J Immunol* 180:3739-45). Data suggest a similar co-stimulatory role for CD27 in NK cells as for T-cells (Takeda et al., 2000, *J Immunol* 164; 1741-1745). The functional effect of CD27 activation on NK cells was established by increased NK mediated killing of CD70-expressing tumor cells. CD27-mediated NK cell activation also promoted the generation of $CD8^+$ anti-tumor immunity (Aulwurm et al., 2006, *Int J Cancer* 11S:1728-1735; Kelly et al., 2002, *Nat Immunol* 3:83-90). Recently, NKT cells were shown to promote $CD8^+$ T cell immunity by induction of CD70 on dendritic cells (Taraban et al., 2008, *J Immunol* 139:1589-96).

In addition, CD27 is highly expressed on tumor cells derived from non-Hodgkin's lymphomas and chronic lymphocytic leukemias (Ranheim et al., 1995, *Blood* 85:3556-3565; van Oers et al., 1993, *Blood* 82:3430-3436). Soluble CD27 is used as a serum marker for lymphoid malignancy (Van Oers et al., 1993, *Blood* 82:3430-6).

In the research that led to the present invention it was found that the hCD27.15 mAb stimulates the proliferation and/or survival of $CD27^+$ cells. Enhanced proliferation and/or survival of $CD27^+$ cells forms the basis of different therapeutic uses. Monoclonal antibodies that activate CD27 are known. Two activating anti-human CD27 antibodies have been described (Van Lier et al., 1987, *J. Immunol.* 1987, 139:1589-96; Kobata et al., 1994, *J. Immunol.* 153:5422-5432). In addition, activating anti-mouse CD27 antibodies have been described (French et al., 2007, *Blood* 109:4810-15; WO 2008/051424; Sakanishi and Yagita, 2010, *Biochem. Biophys. Res. Comm.* 393:829-835). hCD27.15 is a unique anti-human antibody, which is, in contrast to 1A4 and 9F4 able to activate human CD27 more effectively than its ligand CD70. These characteristics of hCD27.15 result in a significantly increased effect on proliferation of $CD8^+$ and $CD^+$ T-cells as compared to 1A4, 9F4 and Fc-CD70. Administration of hCD27.15 alone or in combination with other agents to a human being can for example be used in the treatment of cancer.

Citation or identification of any document in this application is not an admission that such document is available as prior art to the present invention.

SUMMARY OF THE INVENTION

The invention thus relates to binding compounds that bind to the same epitope as hCD27.15. The hybridoma producing hCD27.15 was deposited with the ATCC on Jun. 2, 2010 and given the deposit accession number PTA-11008.

The invention relates to all molecules that bind the same epitope as it was found that binding to this particular epitope stimulates the proliferation and/or survival of a $CD27^+$ cell.

In one embodiment, the invention relates to binding compounds, which bind to CD27 and may comprise:
- an antibody heavy chain variable region which may comprise at least one CDR selected from the group consisting of SEQ ID NOs: 5, 6 and 7, or a variant of any of said sequences; and/or
- an antibody light chain variable region which may comprise at least one CDR selected from the group consisting of SEQ ID NOs: 8, 9 and 10, or a variant of any of said sequences.

In one embodiment, the invention relates to binding compounds, which bind to CD27 and may comprise:
- an antibody heavy chain variable region which may comprise a combination of CDRs selected from the group consisting of SEQ ID NOs: 5, 6 and 7, SEQ ID NOs: 5 and 7, SEQ ID NOs: 6 and 7, and SEQ ID NOs: 5 and 6, or a variant of any of said sequences; and/or
- an antibody light chain variable region which may comprise a combination of CDRs selected from the group consisting of SEQ ID NOs: 8, 9 and 10, SEQ ID NOs: 8 and 10, SEQ ID NOs: 9 and 10, and SEQ ID NOs: 8 and 9, or a variant of any of said sequences.

In one embodiment, the invention relates to any combination of heavy and light chain variable regions having the combinations of CDRs disclosed above, in particular the following combinations:

SEQ ID NOs: 5, 6 and 7 with SEQ ID NOs: 8, 9 and 10,
SEQ ID NOs: 5, 6 and 7 with SEQ ID NOs: 8 and 10,
SEQ ID NOs: 5, 6 and 7 with SEQ ID NOs: 9 and 10,
SEQ ID NOs: 5, 6 and 7 with SEQ ID NOs: 8 and 9
SEQ ID NOs: 5 and 7 with SEQ ID NOs: 8, 9 and 10,
SEQ ID NOs: 5 and 7 with SEQ ID NOs: 8 and 10,
SEQ ID NOs: 5 and 7 with SEQ ID NOs: 9 and 10,
SEQ ID NOs: 5 and 7 with SEQ ID NOs: 8 and 9,
SEQ ID NOs: 6 and 7 with SEQ ID NOs: 8, 9 and 10,
SEQ ID NOs: 6 and 7 with SEQ ID NOs: 8 and 10,
SEQ ID NOs: 6 and 7 with SEQ ID NOs: 9 and 10,
SEQ ID NOs: 6 and 7 with SEQ ID NOs: 8 and 9,
SEQ ID NOs: 5 and 6 with SEQ ID NOs: 8, 9 and 10,
SEQ ID NOs: 5 and 6 with SEQ ID NOs: 8 and 10,
SEQ ID NOs: 5 and 6 with SEQ ID NOs: 9 and 10,
SEQ ID NOs: 5 and 6 with SEQ ID NOs: 8 and 9.

In one embodiment, the invention relates to binding compounds, which bind to CD27 and may comprise:
an antibody heavy chain variable region which may comprise the CDRs of SEQ ID NOs: 5, 6 and 7, or a variant of any of said sequences; and/or
an antibody light chain variable region which may comprise the CDRs of SEQ ID NOs: 8, 9 and 10, or a variant of any of said sequences.

In one embodiment, the binding molecule binds to CD27 and comprises:
a heavy chain variable region which may comprise the amino acid sequence of SEQ ID NO: 3 and a light chain variable region which may comprise the amino acid sequence of SEQ ID NO: 4.

In one embodiment, the binding compound is monoclonal antibody hCD27.15 as produced by hybridoma hCD27.15 (deposit accession number PTA-11008) or a humanized version thereof.

In one embodiment the binding compound is a fragment, variant or derivative of an antibody.

According to a further aspect thereof, the invention relates to an isolated polynucleotide encoding a binding compound of the invention. The invention further relates to an expression vector which may comprise the said polynucleotide and a host cell which may comprise the expression vector. In one embodiment, the invention relates to the isolated polynucleotides of SEQ ID NOs 1 and 2, which encode the heavy and light chain of hCD27.15, respectively.

In one embodiment, the binding compound:
binds human CD27 with a $K_D$ of about 100 nM or lower; and
blocks binding of human CD27 to human CD70 with an $IC_{50}$ of about 10 nM or lower.

In one embodiment, the invention relates to a binding compound which competes for a binding epitope on human CD27 with any of the above binding compounds and has one or more of the following characteristics:
binds human CD27 with a $K_D$ of about 100 nM or lower;
binds to human CD27 with about the same $K_D$ as an antibody having a heavy chain which may comprise the amino acid sequence of SEQ ID NO: 3 and a light chain which may comprise the amino acid sequence of SEQ ID NO: 4;
blocks binding of human CD27 to human CD70 with an $IC_{50}$ of about 10 nM or lower.

The binding compound may be any one of the following:
a chimeric antibody or a fragment thereof;
a human antibody or a fragment thereof;
a humanized antibody or a fragment thereof; or
an antibody fragment selected from the group consisting of Fab, Fab', Fab'-SH, Fv, scFv, F(ab')$_2$, bispecific mAb and a diabody.

According to another aspect thereof the invention relates to an isolated polynucleotide encoding the binding compound of the invention. In one embodiment, the isolated polynucleotide comprises SEQ ID NOs 1 and 2, which encode the heavy and light chain of hCD27.15.

The invention also relates to an expression vector which may comprise the polynucleotide and to a host cell which may comprise the expression vector or the polynucleotide.

According to a further aspect thereof, the invention relates to a method of producing a binding compound of the invention, which method comprises:
(a) culturing host cell which may comprise an expression vector that comprises a polynucleotide encoding a binding compound of the invention under the control of suitable regulatory sequences in culture medium under conditions wherein the polynucleotide is expressed, thereby producing polypeptides which may comprise the light and heavy chain variable regions; and
(b) recovering the polypeptides from the host cell or culture medium.

The invention further relates to a composition which may comprise a binding compound in combination with a pharmaceutically acceptable carrier or diluent. Such composition in one embodiment may comprise more than one binding compound. In one embodiment, the composition comprises one or more other active compounds in addition to the one or more binding compounds of the invention. Such combination compositions may be used for combination therapy, for example in the treatment of cancer. In that case the binding compound is combined with one or more of the usual anticancer drugs. For other combination therapies other additional active compounds are used. For combination therapy it is not obligatory to have the two or more active compounds in the same composition. Thus, also part of the invention is the combined or subsequent use of the binding compounds and the other active compound, wherein the binding compound and the other active compound are administered simultaneously or subsequently.

The invention further relates to the use of the binding compounds in therapy and diagnosis and for other, non-therapeutic purposes.

In one embodiment, the therapy comprises stimulation of proliferation and/or survival of CD27$^+$ cells. In one embodiment, the therapy comprises the treatment of cancer. In one embodiment, the therapy comprises the treatment of an autoimmune disease.

The binding compound of the invention when used in non-therapeutic applications may for example be applied in techniques such as flow-cytometry, Western blotting, enzyme-linked immunosorbent assay (ELISA) and immunohistochemistry.

In the following these binding compounds will be referred to as "binding compounds based on hCD27.15". This phrase is intended to encompass every compound that binds to the epitope of CD27 recognized by hCD27.15 as described above. Such compounds may be antibodies that have one or more of the CDR regions of hCD27.15 or fragments, variants or derivatives thereof, or the monoclonal antibody hCD27.15 or a humanized version thereof or other molecules that are capable of binding to this epitope.

In one embodiment, the therapy of the invention comprises targeting CD27$^+$ CD$^+$ or CD8$^+$ T cell subsets such as Tregs, Th17 cells or Th1 cells with a binding compound based on hCD27.15, in particular the hCD27.15 mAb.

Targeting these CD27+ cells with binding compounds based on hCD27.15, in particular the hCD27.15 mAb, will direct the nature of CD4'T cell cytokine production and CD+ T cell help for CD8+ T cell responses, which is beneficial in treating various disease situations, including cancer and auto-immunity. Examples are formed by, but not restricted to lymphocyte derived tumors such as non-Hodgkin's lymphoma, Chronic Lymphocytic leukemias; solid tumors like pancreatic, colon and prostate carcinomas. For this purpose, hCD27.15 may be dosed directly to subjects, alone or in combination with other anti-cancer agents. Examples of use in autoimmunity include, but are not restricted to Rheumatoid Arthritis, Systemic Lupus Erythematosus and Psoriasis.

In addition, the therapy may be directed to infections, such as viral and microbial infections. Examples include, but are not restricted to administering hCD27.15 alone or in combination with other anti-infective drugs to a subject who has been infected with influenza virus or CMV virus.

In one embodiment, stimulations of the immune system with binding compounds based on hCD27.15, in particular the hCD27.15 mAb, may be used to increase vaccine responses. Non-limiting examples of vaccines that may be used in combination with hCD27.15 stimulation include DNA-, cell-based or peptide-based vaccines that are designed to elicit a CD8+ T cell response to cancer or infectious agents. For this purpose, binding compounds based on hCD27.15, in particular the hCD27.15 antibody, may be administered before vaccination, at an appropriate time after vaccination, or be formulated into the vaccine.

Current state of the art technologies allow the isolation of CD27+ cells and the isolation of different cellular subsets. After stimulation of such isolated subsets of cells outside of the body of the patient with hCD27.15, they may subsequently be adoptively transferred to the patient or another patient. In one embodiment, the subset of cells is formed by CD27+ regulatory T-cells (Tregs), which may be isolated from patients suffering from autoimmune disease and which have been shown to demonstrate superior suppressive characteristics.

The monoclonal antibody hCD27.15 promotes the proliferation and/or survival of CD27+ cells. State of the art technologies use the isolation of (subsets of) cells from a wide range of body fluids and organs. Based on hCD27.15 stimulatory characteristics, binding compounds based on hCD27.15 may be used in in vitro cellular systems to promote proliferation and/or survival of CD27+ cells. A non-limiting example forms Tregs, which have been demonstrated to have a short lifespan. Other examples form memory B-cells and activated T-cells.

Stimulation and proliferation of CD27+ cells using binding compounds based on hCD27.15, in particular the hCD27.15 mAb, may thus be used to increase the Treg populations ex vivo, which may be adoptively transferred to the patient to suppress the hyper-activated immune system of the patient. Such approach could be used to treat patients who suffer from an activated immune system. This strategy may thus for example be used to prevent transplant rejections and to treat autoimmune and inflammatory diseases.

Another example is the isolation of tumor-associated lymphocytes. Such lymphocytes harbor anti-tumor activity, but are suppressed in activation by the tumor and its environment. Isolation of these lymphocytes, subsequent activation outside of the body using binding compounds based on hCD27.15, in particular the hCD27.15 mAb, and adoptive transfer to the patient is expected to deliver a proficient anti-tumor response.

The binding compounds based on hCD27.15, in particular the hCD27.15 antibody, may also be applied in vivo to target CD27+ tumor cells. The non-modified binding compounds based on hCD27.15, in particular the hCD27.15 antibody, may for example be injected into patients with a CD27+ malignancy to elicit antibody-dependent cytotoxicity or other immune effector mechanisms. The binding compounds based on hCD27.15, in particular the hCD27.15 antibody, may also be conjugated with a toxin or other appropriate drug to kill the targeted CD27+ tumor cells.

The binding compounds based on hCD27.15 may also be useful in diagnostic assays, e.g., for detecting expression of CD27 on specific cells, tissues, or in serum. For diagnostic applications, the binding compounds based on hCD27.15 typically will be labeled (either directly or indirectly) with a detectable moiety. Numerous labels are available which may be generally grouped into the following categories: biotin, fluorochromes, radionucleotides, enzymes, iodine, and biosynthetic labels.

Soluble CD27 present in the serum and other body fluids of a range of different patients has been shown to correlate with disease severity of the patients. For example, patients suffering from chronic lymphocytic leukemia, acute lymphoblastic leukemia and non-Hodgkin's lymphoma demonstrated increased serum levels of soluble CD27. Based on the demonstrated binding characteristics of hCD27.15, binding compounds based on hCD27.15 may be used as a diagnostic tool to detect soluble CD27 in the body fluids.

The binding compounds based on hCD27.15 of the present invention may be employed in any known assay method, such as competitive binding assays, direct and indirect sandwich assays, and immunoprecipitation assays. Zola, Monoclonal Antibodies. A Manual of Techniques, pp. 147-158 (CRC Press, Inc. 1987).

The binding compounds based on hCD27.15 may also be used for in vivo diagnostic assays. Generally, the binding compound is labeled with a radionuclide so that the antigen or cells expressing it may be localized using immunoscintigraphy or positron emission tomography.

According to another aspect of the invention, the binding compounds have other, non-therapeutic uses. The non-therapeutic uses for these binding compounds based on hCD27.15 include flow cytometry, western blotting, enzyme linked immunosorbant assay (ELISA) and immunohistochemistry.

The binding compounds based on hCD27.15 of this invention may for example be used as an affinity purification reagent via immobilization to a Protein A-Sepharose column.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with the ATCC, under deposit accession number PTA-11008 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 6 shows the variable region sequences of hCD27.15. Panel A and B show the amino acid sequences of the heavy and light chain variable sequence of hCD27.15, respectively.

DETAILED DESCRIPTION OF THE INVENTION

Figure 1:
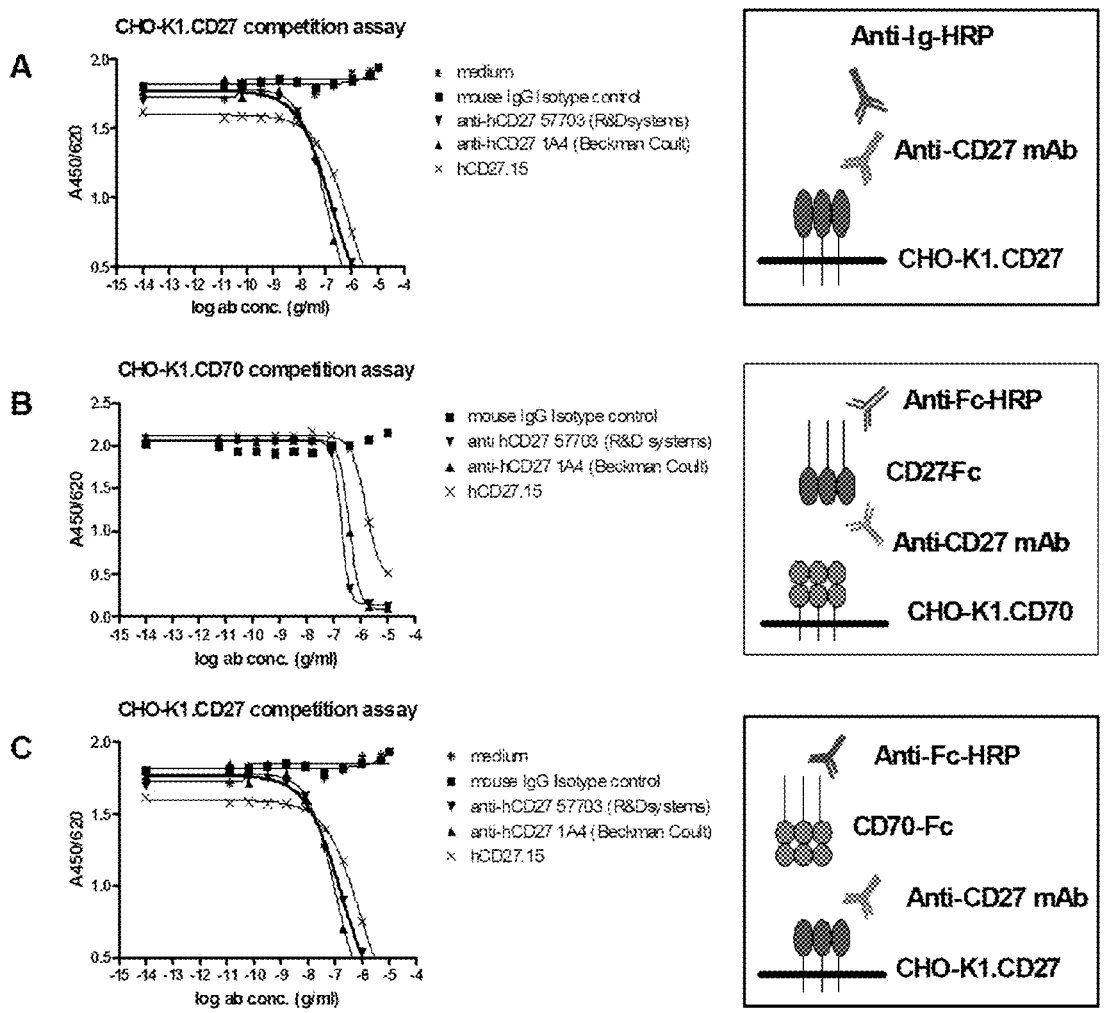
FIG. 1. Characterization of anti-hCD27 antibody. A. Binding of hCD27.15 to CHO-K1 that were stably transfected with pCI-neo-hCD27 (CHO-K1.CD27). Anti-hCD27 57703 (R&D systems) and anti-hCD27 1A4 (Beckman Coulter) are positive controls. Antibodies were not reactive with CHO-K1 control cells (data not shown). B. Effect of hCD27.15 on binding of soluble recombinant hCD27-Fc fusion protein to CHO-K1 cells that had been stably transfected with pCI-neo-hCD70 (CHO-K1.CD70). C. Effect of hCD27.15 on binding of recombinant hCD70-mCD8 fusion protein to CHO-K1.CD27.

The term "antibody" refers to any form of antibody that exhibits the desired biological activity, such as inhibiting binding of a ligand to its receptor, or by inhibiting ligand-induced signaling of a receptor. In the present case the biological activity comprises agonist activity on CD27. Thus, "antibody" is used in the broadest sense and specifically covers, but is not limited to, monoclonal antibodies (including full length monoclonal antibodies), polyclonal antibodies, and multispecific antibodies (e.g., bispecific antibodies).

"Antibody fragment" and "antibody binding fragment" mean antigen-binding fragments and analogues of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Examples of antibody fragments include, but are not limited to, Fab, Fab', F(ab')2, and Fv fragments; diabodies; linear antibodies; single-chain antibody molecules, e.g., sc-Fv, unibodies (technology from Genmab); nanobodies (technology from Domantis); domain antibodies (technology from Ablynx); and multispecific antibodies formed from antibody fragments. Engineered antibody variants are reviewed in Bolliger and Hudson, 2005, Nat. Biotechnol. 23:1126-1136.

An "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments which may comprise the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond may be formed between the two heavy chains of two Fab' fragments to form a F(ab')$_2$ molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments which may comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun, 1994, The Pharmacology of Monoclonal Antibodies, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments may comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al., 1993, Proc. Natl. Acad. Sci. USA 90:6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

As used herein antibody hCD27.15 is a mouse antibody wherein the heavy chain has the variable region sequence of SEQ ID NO: 3 and is joined to a IgG1 constant region and the light chain has the variable region sequence of SEQ ID NO: 4 and is joined to the κ constant region. The hybridoma producing the hCD27.15 antibody was deposited with ATCC on Jun. 2, 2010 under number PTA-11008.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered as described herein. In another embodiment, an antibody fragment, for example one that comprises the Fe region, retains at least one of the biological functions normally associated with the Fe region when present in an intact antibody, such as FcRn binding, antibody half life modulation, ADCC (antibody dependent cellular cytotoxicity) function, and/or complement binding (for example, where the antibody has a glycosylation profile necessary for ADCC function or complement binding).

The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855).

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody may comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also may comprise at least a portion of an immunoglobulin constant region (Fc), typically that of a human immunoglobulin. The humanized forms of rodent antibodies may essentially comprise the same CDR sequences of the parental rodent antibodies, although certain amino acid substitutions may be included to increase affinity, increase stability of the humanized antibody, or for other reasons. However, as CDR loop exchanges do not uniformly result in an antibody with the same binding properties as the antibody of origin, changes in framework residues (FR), residues involved in CDR loop support, might also be introduced in humanized antibodies to preserve antigen binding affinity (Kabat et al., 1991, *J. Immunol.* 147:1709).

The term "antibody" also includes "fully human" antibodies, i.e., antibodies that may comprise human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that may comprise only mouse or rat immunoglobulin sequences, respectively. A fully human antibody may be generated in a human being, in a transgenic animal having human immunoglobulin germline sequences, by phage display or other molecular biological methods. Also, recombinant immunoglobulins may also be made in transgenic mice. See Mendez et al., 1997, Nature Genetics 15:146-156. See also Abgenix and Medarex technologies.

The binding compounds of the present invention also include antibodies with modified (or blocked) Fc regions to provide altered effector functions. See, e.g. U.S. Pat. No. 5,624,821; WO2003/086310; WO2005/120571; WO2006/0057702; Presta, 2006, Adv. Drug Delivery Rev. 58:640-656. Such modification may be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc may also alter the half-life of antibodies in therapeutic antibodies, and a longer half-life would result in less frequent dosing, with the concomitant increased convenience and decreased use of material. See Presta, 2005, *J. Allergy Clin. Immunol.* 116: 731 at 734-35.

The binding compounds of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in the a targeted cell.

The antibodies may also be conjugated (e.g., covalently linked) to molecules that improve stability of the antibody during storage or increase the half-life of the antibody in vivo. Examples of molecules that increase the half-life are albumin (e.g., human serum albumin) and polyethylene glycol (PEG). Albumin-linked and PEGylated derivatives of antibodies may be prepared using techniques well known in the art. See, e.g. Chapman, 2002, Adv. Drug Deliv. Rev. 54:531-545; Anderson and Tomasi, 1988, J. Immunol. Methods 109:37-42; Suzuki et al., 1984, Biochim. Biophys. Acta 788:248-255; and Brekke and Sandlie, 2003, Nature Rev. 2:52-62.

Binding compounds, in particular antibodies, used in the present invention will usually bind with at least a KD of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M. See, e.g. Presta, et al., 2001, Thromb. Haemost. 85:379-389; Yang, et al., 2001, Crit. Rev. Oncol. Hematol. 38:17-23; Carnahan, et al., 2003, Clin. Cancer Res. (Suppl.) 9:3982s-3990s. Antibody affinities may be determined using standard analysis.

The term "hypervariable region," as used herein, refers to the amino acid residues of an antibody which are responsible for antigen-binding. The hypervariable region may comprise amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain (see Kabat et al., 1991, Sequences of proteins of Immunological Interest, 5th Ed. Public Health Service, National Institutes of Health, Bethesda, Md.) and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain (see Chothia and Leskl, 1987, J. Mol. Biol. 196:901-917). "Framework" or "FR" residues are those variable domain residues other than the hypervariable region residues as herein defined.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example. The monoclonal antibodies herein specifically include "chimeric" antibodies.

As used herein, the term "immune cell" includes cells that are of hematopoietic origin and that play a role in the immune response. Immune cells include lymphocytes, such as B cells and T cells, natural killer cells, myeloid cells, such as monocytes, macrophages, eosinophils, mast cells, basophils, and granulocytes.

As used herein, an "immunoconjugate" refers to an anti-CD27 antibody, or a fragment thereof, conjugated to a therapeutic moiety, such as a bacterial toxin, a cytotoxic drug or a radiotoxin. Toxic moieties may be conjugated to antibodies of the invention using methods available in the art.

As used herein, a sequence "variant" refers to a sequence that differs from the disclosed sequence at one or more amino acid residues but which retains the biological activity of the resulting molecule. The invention relates to variants of binding compounds based on hCD27.15 and to variants of hCD27.15.

"Conservatively modified variants" or "conservative amino acid substitution" refers to substitutions of amino acids that are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth below as follows:
Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the term "about" refers to a value that is within an acceptable error range for the particular value as determined by one of ordinary skill in the art, which will depend in part on how the value is measured or determined, i.e. the limitations of the measurement system. For example, "about" may mean within 1 or more than 1 standard deviation per the practice in the art. Alternatively, "about" or "comprising essentially of" may mean a range of up to 20%. Furthermore, particularly with respect to biological systems or processes, the terms may mean up to an order of magnitude or up to 5-fold of a value. When particular values are provided in the application and claims, unless otherwise stated, the meaning of "about" or "comprising essentially of" should be assumed to be within an acceptable error range for that particular value.

"Specifically" binds, when referring to a ligand/receptor, antibody/antigen, or other binding pair, indicates a binding reaction which is determinative of the presence of the protein, e.g., CD27, in a heterogeneous population of proteins and/or other biologics. Thus, under designated conditions, a specified ligand/antigen binds to a particular receptor/antibody and does not bind in a significant amount to other proteins present in the sample.

"Administration", "therapy" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration", "therapy" and "treatment" may refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration", "therapy" and "treatment" also mean in vitro and ex vivo treatments, e.g., of a cell, by a reagent, diagnostic, binding composition, or by another cell.

Monoclonal antibodies may be made according to knowledge and skill in the art of injecting test subjects with human CD27 antigen and then generating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

Antibodies or antibody fragments may be isolated from antibody phage libraries generated using the techniques described in McCafferty et al., 1990, Nature, 348:552-554. Clackson et al., 1991, Nature, 352:624-628, and Marks et al., 1991, J. Mol. Biol. 222:581-597 describe the isolation of murine and human antibodies, respectively, using phage libraries. Subsequent publications describe the production of high affinity (nM range) human antibodies by chain shuffling (Marks et al., 1992, Bio/Technology, 10:779-783), as well as combinatorial infection and in vivo recombination as a strategy for constructing very large phage libraries (Waterhouse et al., 1993, Nuc. Acids. Res. 21:2265-2266). Thus, these techniques are viable alternatives to traditional monoclonal antibody hybridoma techniques for isolation of monoclonal antibodies.

The antibody DNA also may be modified, for example, by substituting the coding sequence for human heavy- and light-chain constant domains in place of the homologous murine sequences (U.S. Pat. No. 4,816,567; Morrison, et al., 1984, Proc. Natl. Acad. Sci. USA, 81:6851), or by covalently joining to the immunoglobulin coding sequence all or part of the coding sequence for non-immunoglobulin material (e.g., protein domains). Typically such non-immunoglobulin material is substituted for the constant domains of an antibody, or is substituted for the variable domains of one antigen-combining site of an antibody to create a chimeric bivalent antibody which may comprise one antigen-combining site having specificity for an antigen and another antigen-combining site having specificity for a different antigen.

A humanized antibody has one or more amino acid residues from a source that is non-human. The non-human amino acid residues are often referred to as "import" residues, and are typically taken from an "import" variable domain. Humanization may be performed generally following the method of Winter and co-workers (Jones et al., 1986, Nature 321:522-525; Riechmann et al., 1988, Nature, 332: 323-327; Verhoeyen et al., 1988, Science 239:1534-1536), by substituting rodent CDRs or CDR sequences for the corresponding sequences of a human antibody. Accordingly, such "humanized" antibodies are antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., 1987, J. Immunol. 151:2296; Chothia et al., 1987, J. Mol. Biol. 196:901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA* 89:4285; Presta et al., 1993, *J. Immunol.* 151:2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues may be selected and combined from the recipient and import sequences so that the desired antibody characteristic, such as increased affinity for the target antigen(s), is achieved. In general, the CDR residues are directly and most substantially involved in influencing antigen binding.

Humanization of antibodies is a straightforward protein engineering task. Nearly all murine antibodies may be humanized by CDR grafting, resulting in the retention of antigen binding. See, Lo, Benny, K. C., editor, in Antibody Engineering: Methods and Protocols, volume 248, Humana Press, New Jersey, 2004.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA* 90:2551; Jakobovits et al., 1993, *Nature* 362:255-258; Bruggermann et al., 1993, *Year in Immunology* 7:33; and Duchosal et al., 1992, *Nature* 355:258. Human antibodies may also be derived from phage-display libraries (Hoogenboom et al., 1991, *J. Mol. Biol.* 227:381; Marks et al., *J. Mol. Biol.* 1991, 222:581-597; Vaughan et al., 1996, *Nature* Biotech 14:309).

Amino acid sequence variants of humanized anti-CD27 antibodies are prepared by introducing appropriate nucleotide changes into the humanized anti-CD27 antibodies' DNAs, or by peptide synthesis. Such variants include, for example, deletions from, and/or insertions into, and/or substitutions of, residues within the amino acid sequences shown for the humanized anti-CD27 antibodies. Any combination of deletion, insertion, and substitution is made to arrive at the final construct, provided that the final construct possesses the desired characteristics. The amino acid changes also may alter post-translational processes of the humanized anti-CD27 antibodies, such as changing the number or position of glycosylation sites.

A useful method for identification of certain residues or regions of the humanized anti-CD27 antibodies polypeptides that are preferred locations for mutagenesis is called "alanine scanning mutagenesis," as described by Cunningham and Wells, 1989, *Science* 244:1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with CD27 antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-CD27 antibodies' variants are screened for the desired activity.

Ordinarily, amino acid sequence variants of the humanized anti-CD27 antibodies will have an amino acid sequence having at least 75% amino acid sequence identity with the original mouse antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology. The percentage of identity between two sequences may be determined with computer application such as SeqMan II (DNAstar Inc, version 5.05). Using this program two sequences may be aligned using the optimal alignment algorithm of Smith and Waterman (1981) (Journal of Molecular Biology 147:195-197). After alignment of the two sequences the percentage identity may be calculated by dividing the number of identical nucleotides between the two sequences by the length of the aligned sequences minus the length of all gaps.

Antibodies having the characteristics identified herein as being desirable in humanized anti-CD27 antibodies may be screened for increased biologic activity in vitro or suitable binding affinity. To screen for antibodies that bind to the epitope on human CD27, a routine cross-blocking assay such as that described in Antibodies, A Laboratory Manual, Cold Spring Harbor Laboratory, Ed Harlow and David Lane (1988), may be performed. Antibodies that bind to the same epitope are likely to cross-block in such assays, but not all cross-blocking antibodies will necessarily bind at precisely the same epitope since cross-blocking may result from steric hindrance of antibody binding by antibodies at overlapping epitopes, or even nearby non-overlapping epitopes.

Alternatively, epitope mapping, e.g., as described in Champe et al., 1995, *J. Biol. Chem.* 270:1388-1394, may be performed to determine whether the antibody binds an epitope of interest. "Alanine scanning mutagenesis," as described by Cunningham and Wells, 1989, *Science* 244: 1081-1085, or some other form of point mutagenesis of amino acid residues in human CD27 may also be used to determine the functional epitope for anti-CD27 antibodies of the present invention. Additional antibodies binding to the same epitope as an antibody of the present invention may be obtained, for example, by screening of antibodies raised against CD27 for binding to the epitope, or by immunization of an animal with a peptide which may comprise a fragment of human CD27 which may comprise the epitope sequences. Antibodies that bind to the same functional epitope might be expected to exhibit similar biological activities, such as blocking receptor binding, and such activities may be confirmed by functional assays of the antibodies.

Antibody affinities may be determined using standard analysis. Preferred binding compounds such as e.g. humanized antibodies are those that bind human CD27 with a Kd value of no more than about $1 \times 10^{-7}$; preferably no more than about $1 \times 10^{-8}$; more preferably no more than about $1 \times 10^{-9}$; and most preferably no more than about $1 \times 10^{-10}$ or even $1 \times 10^{-11}$ M.

The humanized antibody may be selected from any class of immunoglobulins, including IgM, IgG, IgD, IgA, and IgE. Preferably, the antibody is an IgG antibody. Any isotype of IgG may be used, including IgG1, IgG2, IgG3, and IgG4. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain may be used in the compositions and methods herein. Specifically, kappa, lambda, or variants thereof are useful in the present compositions and methods.

The antibodies and antibody fragments of the invention may also be conjugated with cytotoxic payloads such as cytotoxic agents or radionucleotides such as $^{99}TC$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}Cu$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$. Such antibody conjugates may be used in immunotherapy to selectively target and kill cells expressing a target (the antigen for that antibody) on their surface. Exemplary cytotoxic agents include ricin, vinca alkaloid, methotrexate, Psuedomonas exotoxin, saporin, diphtheria toxin, cisplatin, doxorubicin, abrin toxin, gelonin and pokeweed antiviral protein.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules or protein molecules of the invention to the various moieties may be employed, including those methods described by Hunter et al., 1962, Nature 144:945; David et al., 1974, Biochemistry 13:1014; Pain et al., 1981, J. Immunol. Meth. 40:219; and Nygren, J., 1982, Histochem. and Cytochem. 30:407. Methods for conjugating antibodies and proteins are conventional and well known in the art.

When using recombinant techniques, the antibody may be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., 1992, Bio/Technology 10:163-167 describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris may be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells may be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A may be used to purify antibodies that are based on human Ig.gamma1, Ig.gamma2, or Ig.gamma4 heavy chains (Lindmark et al., 1983, J. Immunol. Meth. 62:1-13). Protein G is recommended for all mouse isotypes and for human .gamma.3 (Guss et al., 1986, EMBO J. 5:1567-1575). The matrix to which the affinity ligand is attached is most often agarose, but other matrices are available. Mechanically stable matrices such as controlled pore glass or poly(styrenedivinyl) benzene allow for faster flow rates and shorter processing times than may be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the glycoprotein may be purified using adsorption onto a lectin substrate (e.g. a lectin affinity column) to remove fucose-containing glycoprotein from the preparation and thereby enrich for fucose-free glycoprotein.

The invention may comprise pharmaceutical formulations of a CD27 binding compound. To prepare pharmaceutical or sterile compositions, the binding compound, in particular an antibody or fragment thereof, is admixed with a pharmaceutically acceptable carrier or excipient, see, e.g., Remington's Pharmaceutical Sciences and U.S. Pharmacopeia: National Formulary, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al., 2001, Goodman and Gilman's The Pharmacological Basis of Therapeutics, McGraw-Hill, New York, N.Y.; Gennaro, 2000, Remington: The Science and Practice of Pharmacy, Lippincott, Williams, and Wilkins, New York, N.Y.; Avis, et al. (eds.), 1993, Pharmaceutical Dosage Forms: Parenteral Medications, Marcel Dekker, NY; Lieberman, et al. (eds.), 1990, Pharmaceutical Dosage Forms: Tablets, Marcel Dekker, NY; Lieberman, et al. (eds.), 1990, Pharmaceutical Dosage Forms: Disperse Systems, Marcel Dekker, NY; Weiner and Kotkoskie, 2000, *Excipient Toxicity and Safety*, Marcel Dekker, Inc., New York, N.Y.).

Toxicity and therapeutic efficacy of the binding compound, in particular antibody, compositions, administered alone or in combination with another agent, such as the usual anti-cancer drugs, may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. The data obtained from these cell culture assays and animal studies may be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration and oral administration. Administration of binding compounds such as antibodies, used in the pharmaceutical composition or to practice the method of the present invention may be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternatively, one may administer the binding compound in a local rather than systemic manner, for example, via injection of the binding compound directly into the site of action, often in a depot or sustained release formulation. Furthermore, one may administer the antibody in a targeted drug delivery system.

Guidance in selecting appropriate doses of antibodies, cytokines, and small molecules are available (see, e.g., Wawrzynczak, 1996, *Antibody Therapy*, Bios Scientific Pub. Ltd, Oxfordshire, UK; Kresina (ed.), 1991, *Monoclonal Antibodies, Cytokines and Arthritis*, Marcel Dekker, New York, N.Y.; Bach (ed.), 1993, *Monoclonal Antibodies and Peptide Therapy in Autoimmune Diseases*, Marcel Dekker, New York, N.Y.; Baert, et al., 2003, *New Engl. J. Med.* 348:601-608; Milgrom, et al., 1999, *New Engl. J. Med.* 341:1966-1973; Slamon, et al., 2001, *New Engl. J. Med.* 344:783-792; Beniaminovitz, et al., 2000, *New Engl. J. Med.* 342:613-619; Ghosh, et al., 2003, *New Engl. J. Med.* 348: 24-32; Lipsky, et al., 2000, *New Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al., 2003, *New Engl. J. Med.* 349:427-434; Herold, et al., 2002, *New Engl. J. Med.* 346:1692-1698; Liu, et al., 1999, *J. Neural. Neurosurg. Psych.* 67:451-456; Portielji, et al., 2003, *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with disease and/or a reduction in the severity of such symptoms that will or are expected to develop with said disease. The terms further include ameliorating existing symptoms, preventing additional symptoms, and ameliorating or preventing the underlying causes of such symptoms. Thus, the terms denote that a beneficial result has been conferred on a vertebrate subject with a disease.

As used herein, the term "therapeutically effective amount" or "effective amount" refers to an amount of an anti-CD27 antibody or fragment thereof, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent are well known in the art, see, e.g., Hardman, et al. (eds.), 2001, *Goodman and Gilman's The Pharmacological Basis of Therapeutics*, 10th ed., McGraw-Hill, New York, N.Y.; Poole and Peterson (eds.), 2001, *Pharmacotherapeutics for Advanced Practice: A Practical Approach*, Lippincott, Williams & Wilkins, Phila., Pa.; Chabner and Longo (eds.), 2001, *Cancer Chemotherapy and Biotherapy*, Lippincott, Williams & Wilkins, Phila., Pa.

The pharmaceutical composition of the invention may also contain other agents, including but not limited to a cytotoxic, chemotherapeutic, cytostatic, anti-angiogenic or antimetabolite agents, a tumor targeted agent, an immune stimulating or immune modulating agent or an antibody conjugated to a cytotoxic, cytostatic, or otherwise toxic agent. The pharmaceutical composition may also be employed with other therapeutic modalities such as surgery, chemotherapy and radiation.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Immunization and Selection of Anti-CD27 Antibodies

Immunization of Mice with CD27 cDNA

To isolate antibodies against the human CD27 protein that harbour agonistic activity we hypothesized to find such antibodies among a set of anti-CD27 antibodies, which bind to the ligand binding site. To generate anti-hCD27 antibodies, the cDNA encoding the full length open reading frame of hCD27 was subcloned into the pCI-neo vector (Promega, Madison, Wis.). Expression of the obtained vector was checked by transient transfection of pCI-neo-hCD27 in CHO-K1 cells (American Type Culture Collection, Manassas, Va.) and flow cytometry using 10 µg/ml mouse anti-hCD27 IgG1 (BD Pharmingen #555439), followed by goat anti-mouse IgG1-FITC (1:100) (Southern Biotechnology, Birmingham, Ala.).

Mice were immunized by gene gun immunization using a Helios Gene gun (BioRad, Hercules, Calif.) and DNA coated gold bullets (BioRad) following manufacturer's instructions. Briefly, 1 µm gold particles were coated with pCI-neo-hCD27 cDNA and commercial expression vectors for mouse Flt3L and mouse GM-CSF in a 2:1:1 ratio (both from Aldevron, Fargo, N. Dak.). A total of 1 µg of plasmid DNA was used to coat 500 µg of gold particles.

Specifically, 7-8 weeks old female BALB/C mice were immunized in the ears with a gene gun, receiving 3 cycles of a shot in both ears. Approximately, a 1:4,000 anti-hCD27 titer was detected by cell-ELISA in mouse serum after two DNA immunizations. In the cell-ELISA, all incubation steps were followed by a wash step with PBST (PBS with 0.01% Tween 20). Parental CHO-K1 or CHO-K1.hCD27 cells were seeded (40,000 cells/well) in tissue culture plates and incubated overnight at 37° C. The next day, culture medium was removed and cells were incubated for 1 hour with (dilutions of) mouse serum at 37° C. Next, cells were washed with PBST and incubated for 1 hour at 37° C. with 1:1,000 goat-anti-mouse IgG-HRP (Southern Biotechnology, #1030-05).

Subsequently, cells were washed 6 times with PBST and anti-hCD27 immunoreactivity was visualized with 100 µl OptiEIA TMB substrate (BD Biosciences, Franklin Lake, N.J.). Reactions were stopped with 100 µl 0.5 M $H_2SO_4$ and absorbances were read at 460 and 620 nm. Mice that demonstrated reactivity against hCD27 were immunized for a final, fourth time and sacrificed four days later.

Erythrocyte-depleted spleen cell populations were prepared as described previously (Steenbakkers et al., 1992, *J. Immunol. Meth.* 152:69-77; Steenbakkers et al., 1994, *Mol. Biol. Rep.* 19:125-134) and frozen at −140° C.

Selection of Anti-hCD27 Antibody Producing B Cells

To select B cell clones producing anti-hCD27 antibodies, $1.5 \times 10^7$ erythrocyte-depleted splenocytes were depleted for monocytes. hCD27-specific B-cells were selected by binding on irradiated (3,000 RAD) CHO-K1.hCD27 transfectants, which had grown to confluency in a T25-flask. After extensive washing to delete non-specific B-cells, bound B-cells were collected by Trypsin treatment according to the manufacturer's instructions (Invitrogen, cat. no. 25200-056). Next, B-cells were cultured as described by Steenbakkers et al., 1994, *Mol. Biol. Rep.* 19:125-134. Briefly, selected B-cells were mixed with 7.5% (v/v) T-cell supernatant and 50,000 irradiated (2,500 RAD) EL-4 B5 nursing cells in a final volume of 200 µl DMEM F12/P/S/10% BCS in 96-well flat-bottom tissue culture plates.

On day eight, supernatants were screened for hCD27 reactivity by cell-ELISA as described above. Thirteen hCD27-reactive supernatants were identified and tested for their ability to inhibit the interaction between hCD27 and hCD70. In the cell-ELISA, all incubation steps were followed by a wash step with PBST (PBS with 0.01% Tween 20). Parental CHO-K1 or CHO-K1.hCD27 cells were seeded (40,000 cells/well) in tissue culture plates and incubated overnight at 37° C. The next day, culture medium was removed and cells were incubated for one hour with (dilutions of) mouse serum at 37° C. Next, cells were washed with PBST and incubated for one hour at 37° C. with 1:1,000 goat-anti-mouse IgG-HRP (Southern Biotechnology, #1030-05). Subsequently, cells were washed 6 times with PBST and anti-hCD27 immunoreactivity was visualized with 100 µl TMB Stabilized Chromagen (Invitrogen, cat. no. SB02). Reactions were stopped with 100 µl 0.5 M $H_2SO_4$ and absorbances were read at 460 and 620 nm.

In addition, blocking properties of the supernatants were studied using two competition assays. The CHO-K1.CD27 assay works along the following principles: CHO-K1.CD27 cells were seeded (40,000 cells/well) in a 96-well plate and incubated overnight at 37° C. After medium removal, 50 µl recombinant hCD70 (CD70 (h)-muCD8 fusion Protein (Ancell, cat. no. ANC-537)) (0.5 µg/ml) and 50 µl anti-hCD27 antibody containing supernatant were added. After 1 hour incubation at room temperature, the wells were washed three times with PBST. Next, 100 µl/well Streptavidin-HRP conjugate (BD Pharmingen, cat. no. 554066) (1:5,000) was added and cells were incubated for 1 hour at 37° C. After 6 final washes with PBST the ELISA was developed as outlined above. Positive controls: anti-hCD27, clone 57703 (R&D systems, cat. no. MAB382) and anti-hCD27, clone 1A4 (Beckman Coulter, cat. no. IM2034). The CHO-K1.CD70 assay works along the following principles: CHO-K1.CD70 cells were seeded in a 96 well plate at a density of 40,000 cells/well. The same amount of plates was blocked by adding 300 µl medium/well, and all plates were incubated overnight at 37° C. The following day, the medium-only containing plates were emptied by flicking the plate, and 50 µl/well recombinant soluble hCD27-Fc fusion protein (rhCD27/Fc chimera (0.5 µg/ml) (R&D systems cat. no. 382-CD)) was added. To these plates, 50 µl antibody containing medium/sera or medium was added. After 1 hour incubation at room temperature, the 100 µl rhCD27-Fc/antibody mix was transferred to the CHO-K1/CD70 plate(s) from which the medium had been removed. These plate(s) were incubated for 1 hour at room temperature and then washed three times with PBST. 100 µl anti-human Ig (H+L)-HRP conjugate (1:2,500) was added to every well (Promega, cat. no. W4031) and the cells were incubated for 1 hour at 37° C. After 6 final washes with PBST, the ELISA was developed as outlined above.

Positive controls: anti-hCD27, clone 57703 (R&D systems, cat. no. MAB382) and anti-hCD27, clone 1A4 (Beckman Coulter, cat. no. IM2034).

All supernatants demonstrated to contain antibodies that blocked the interaction between hCD27 and hCD70. Subsequently, the B-cell clones from the hCD27 reactive supernatants were immortalized by mini-electrofusion following published procedures (Steenbakkers et al., 1992, *J. Immunol. Meth.* 152:69-77; Steenbakkers et al., 1994, *Mol. Biol. Rep.* 19:125-34). Specifically, B-cells were mixed with $10^6$ Sp2/0-Ag14 myeloma cells, and serum was removed by washing with DMEM F12 media. Cells were treated with Pronase solution (Calbiochem, cat. no. 4308070.536) for 3 minutes and washed with Electrofusion Isomolar Buffer (Eppendorf, cat. no. 53702). Electrofusions were performed in a 50 µl fusion chamber by an alternating electric field of 30 s, 2 MHz, 400 V/cm followed by a square, high field pulse of 10 µs, 3 kV/cm and again by an alternating electric field of 30 s, 2 MHz, 400 V/cm.

Contents of the chamber were transferred to hybridoma selective medium and plated in a 96-well plate under limiting dilution conditions. On day 12 following the fusions, hybridoma supernatants were screened for hCD27 reactivity and hCD70-blocking activity, as described above. Seven hybridomas secreting antibodies in the supernatant which recognized hCD27 and demonstrated blocking activity were isolated and subcloned by limited dilution to safeguard their integrity. Antibody hCD27.15 was selected for further analysis.

Example 2

Purification and Characterization of Anti-hCD27 Antibodies

Stabilization of Anti-hCD27 Producing Hybridomas and Purification of Anti-hCD27 Antibodies Clonal cell populations were obtained for the hCD27.15 hybridoma by two rounds of limiting dilutions. Stable hybridomas were cultured in serum-free media for 7-10 days; supernatants were harvested and filtered through a 0.22 µM nitrocellulose membrane. Antibodies were purified using Prosep A spin columns according to the manufacturer's instructions (Millipore, cat. no. LSK2ABA60). Buffer was exchanged for PBS using PD-10 gel-filtration columns (GE Healthcare). Antibodies were concentrated with Amicon Ultra-15 centrifugal filter units (Millipore, Billerica, Mass.) and quantified using spectrophotometry. Using a mouse monoclonal antibody isotyping test kit (Roche, #11493027001), the (sub)-isotype of all hCD27 antibodies was determined to be IgG1, Kappa.

Binding Analysis

Cell-based ELISA experiments using purified hCD27 antibodies were performed to determine binding activities of hCD27 to cellularly expressed hCD27. In this cell-ELISA, all incubation steps were followed by a wash step with PEST (PBS with 0.01% Tween 20). CHO-K1.hCD27 cells were seeded (40,000 cells/well) in tissue culture plates and incubated overnight at 37° C. The next day, culture medium was removed and cells were incubated for one hour with (dilutions of) purified antibodies at 37° C. Next, cells were washed with PBST and incubated for one hour at 37° C. with 1:1,000 goat-anti-mouse IgG-HRP (Southern Biotechnology, #1030-05). Subsequently, cells were washed 6 times with PBST and anti-hCD27 immunoreactivity was visualized with 100 µl TMB Stabilized Chromagen (Invitrogen, cat. no. SB02). Reactions were stopped with 100 µl 0.5 M $H_2SO_4$ and absorbances were read at 460 and 620 nm. As shown in FIG. 1A, the different hCD27 antibodies (hCD27.15 and controls) bound to hCD27 with different binding strengths. Calculated $EC_{50}$, representing the concentration at which 50% of the total binding signal is observed are represented in Table 1.

TABLE 1

Overview of KD, $EC_{50}$ and $IC_{50}$ values of hCD27.15 and 1A4CD27 (control).

| | KD × 1E-9 (M) | $EC_{50}$ (ng/ml) | $IC_{50}$ (ng/ml) CHO-K1.CD27 | $IC_{50}$ (ng/ml) CHO-K1.CD70 |
|---|---|---|---|---|
| hCD27.15 | 122 | 686.5 | 864 | 1546 |
| 1A4CD27 | | 33 | 93.7 | 370 |

Blocking properties of the purified antibodies were studied using two competition assays. The CHO-K1.CD70 assay works along the following principles: CHO-K1.CD70 cells were seeded in a 96 well plate at a density of 40,000 cells/well. The same amount of plates was blocked by adding 300 µl medium/well, and all plates were incubated overnight at 37° C. The following day, the medium-only containing plates were emptied by flicking the plate, and 50 µl/well rhCD27-Fc chimera (0.5 µg/ml) (R&D systems cat. no. 382-CD) was added. To these plates, 50 µl of different dilutions of purified hCD27.15 antibodies were added. After 1 hour incubation at room temperature, the 100 µl rhCD27Fc/antibody mix was transferred to the CHO-K1/CD70 plate(s) from which the medium had been removed. These plate(s) were incubated for 1 hour at room temperature and then washed 3 times with PBST. 100 µl anti-human Ig (H+L)-HRP conjugate (1:2,500) was added to every well (Promega, cat. no. W4031) and the plates were incubated for 1 hour at 37° C. After 6 final washes with PBST TMB Stabilized Chromagen (Invitrogen, cat. no. SB02) (100 µl/well) was added and the ELISA was read out as outlined above. Positive controls: anti-hCD27, clone 57703 (R&D systems, cat. no. MAB382) and anti-hCD27, clone 1A4 (Beckman Coulter, cat. no. IM2034). As shown in FIG. 1B, the purified hCD27.15 antibody blocked the binding of rhCD27Fc chimera to CHO-K1.CD70 cells. Calculated $IC_{50}$ values of hCD27.15 and the positive control 1A4, which represent the concentration at which half of the inhibition is observed, are presented in Table 1.

The CHO-K1.CD27 assay works along the following principles: CHO-K1.CD27 cells were seeded (40,000 cells/well) in a 96-well plate and incubated overnight at 37° C. After medium removal, 50 µl recombinant mouse CD70 fusion Protein (Fc-mCD70) (0.5 µg/ml) and 50 µl of different dilutions of purified anti-hCD27 antibodies were added. Fc-mCD70 is a fusion protein of murine CD70 (aa 41-195) fused at the C-terminus of the dimerization domain of human IgG1. A cDNA construct encoding this fusion protein was constructed as described by Rowley and Al-Shamkhani, 2004, *J Immunol* 15:172:6039-46 and used to produce Fc-mCD70 protein in 293T human embryonic kidney cells. The protein was purified by affinity chromatography on Protein A Sepharose (GE Health Care).

After 1 hour incubation at room temperature, the wells were washed 3 times with PBST. Next, 100 µl/well Streptavidin-HRP conjugate (BD Pharmingen, cat. no. 554066) (1:5,000) was added and cells were incubated for one hour at 37° C. After 6 final washes with PBST TMB Stabilized Chromagen (Invitrogen, cat. no. SB02) (100 µl/well) was added. The reaction was stopped by the addition of 100 µl 0.5 M $H_2SO_4$. Absorbencies were read at 460 and 620 nn. Positive controls: anti-hCD27, clone 57703 (R&D systems, cat. no. MAB382) and anti-hCD27, clone 1A4 (Beckman Coulter, cat. no. IM2034). As shown in FIG. 1C, hCD27.15 antibodies blocked the interaction between recombinant human CD70 and CHO-K1.CD27 cells. Calculated $IC_{50}$ values are presented in Table 1.

Kinetic Analysis by Label-Free Surface Plasma Resonance (Biacore)

The binding properties of hCD27.15 antibodies were characterized in more detail using label-free surface plasma resonance using Biacore 2000 equipment. Low amounts of antibodies were coupled to a CM5 sensor chip using amine coupling at pH=4.5, with $R_{max}$ not exceeding 100 RU. This will, in combination with a high flow level (30 µl/min) yield good fits to the 1:1 Langmuir binding model. A concentration series of rhCD27Fc chimera, ranging from 0.016 nM to 1 nM, was injected for 1 minute at 30 µl/min. The dissociation was monitored for 5 minutes. The running buffer is HEPES-buffered saline with 3 mM EDTA and 0.005% P20 (HBS-EP), pH 7.4. Combination plots were made by subtraction of the signal obtained at the blank flow cell, using BIAeval 3.2. The sensor grams were fitted to a 1:1 Langmuir binding model. Antibody hCD27.15 shows a fast association and dissociation, resulting in a moderate affinity. The calculated $K_D$ values are presented in Table 1.

Species Cross-Reactivity

Binding of hCD27 antibodies to mouse CD27 was determined using MCF-7 breast carcinoma cells that had been retrovirally transduced to stably express the full length cDNA encoding human CD27 or mouse CD27. Empty vector-transduced cells served as a control. Binding of the antibodies was tested by flow cytometric analysis, with validated agonistic anti-hCD27 antibodies 1A4 and CLB CD27/1; and anti-mouse CD27 LG.3A10 (Gravestein et al., 1995, Int Immunol. 7:551-7) as positive controls. These commercially available anti-hCD27 antibodies, which have been reported to harbor agonistic activities, were obtained as described in Table 2.

TABLE 2 commercially available agonistic anti-CD27 antibodies.

| Antibody | Company | Cat no. |
| --- | --- | --- |
| 9F4 (CLB-CD27/1) | Pelicluster | M1455 |
| 1A4 | Beckman Coulter | IM2034 |

The hCD27.15 antibodies bound to human CD27, but not to mouse CD27 as expressed on the MCF-7 cells.

The binding site of the hCD27.15 antibody was characterized and compared with the commercially available agonistic antibodies 9F4 and 1A4 using a cross-competition Biacore assay. Using common amine coupling at pH 4.5, flow cells were immobilized at 25 µg/ml of each antibody to a high immobilization level. Next, multi flow cell injections of 1 nM of rhCD27Fc chimera (R&D systems, cat. no. 382-CD) with a speed of 5 µl/min were followed by 10 nM of the second antibody. The anti-hCD27 antibody hCD27.15 of the invention and the two known agonistic antibodies (1A4 and 9F4) were used as a primary (immobilized) or secondary (free) antibody. Agonistic anti-CD27 antibody 1A4 was only used as a second antibody and was not immobilized because of the presence of BSA in the buffer. Fc-mCD70 is a fusion protein of murine CD70 (aa 41-195) fused at the C-terminus of the dimerization domain of human IgG1. A cDNA construct encoding this fusion protein was constructed as described by Rowley and Al-Shamkhani, 2004, J Immunol 15:172:6039-46 and used to produce Fc-mCD70 protein in 293T human embryonic kidney cells. The protein was purified by affinity chromatography on Protein A Sepharose (GE Health Care).

All flow cells were regenerated by a 6-second injection of 10 mM HCl at 50 µl/min. An increase in signal upon injection of the second antibody means that the second antibody can still bind and that the primary and secondary bind to different binding sites. If not, it suggests that both antibodies recognize the same epitope of hCD27, have overlapping epitopes, or can not bind at the same time due to steric hindrance. As shown in Table 3 the hCD27.15 and control antibodies can be divided into different binding groups.

TABLE 3

Cross-competition assay using Biacore to determine binding sites of the different anti-hCD27 antibodies (including agonistic antibodies 1A4 and 9F4) and Fc-mCD70.

| | immobilized | | | |
| --- | --- | --- | --- | --- |
| free | hCD27.15 | 9F4 | 1A4 | Fc-mCD70 |
| hCD27.15 | | − | − | − |
| 9F4 | − | | + | − |
| 1A4 | n.d. | n.d. | | n.d. |
| Fc-mCD70 | + | + | − | |

First, the different anti-hCD27 antibodies were immobilized on the CM5 chip (referred to as 'immobilized'), after binding of rhCD27-Fc chimera binding (R&D systems, cat. no. 382-CD) a second antibody was injected (referred to as 'free').
Based on this checkerboard analysis the antibodies were divided in seven (A-G) epitome groups. '+' indicates simultaneous binding, while '−' indicated binding of the second antibody is not possible after capture by the first antibody.
nd indicates, not determined.

Example 3

Figure 2:
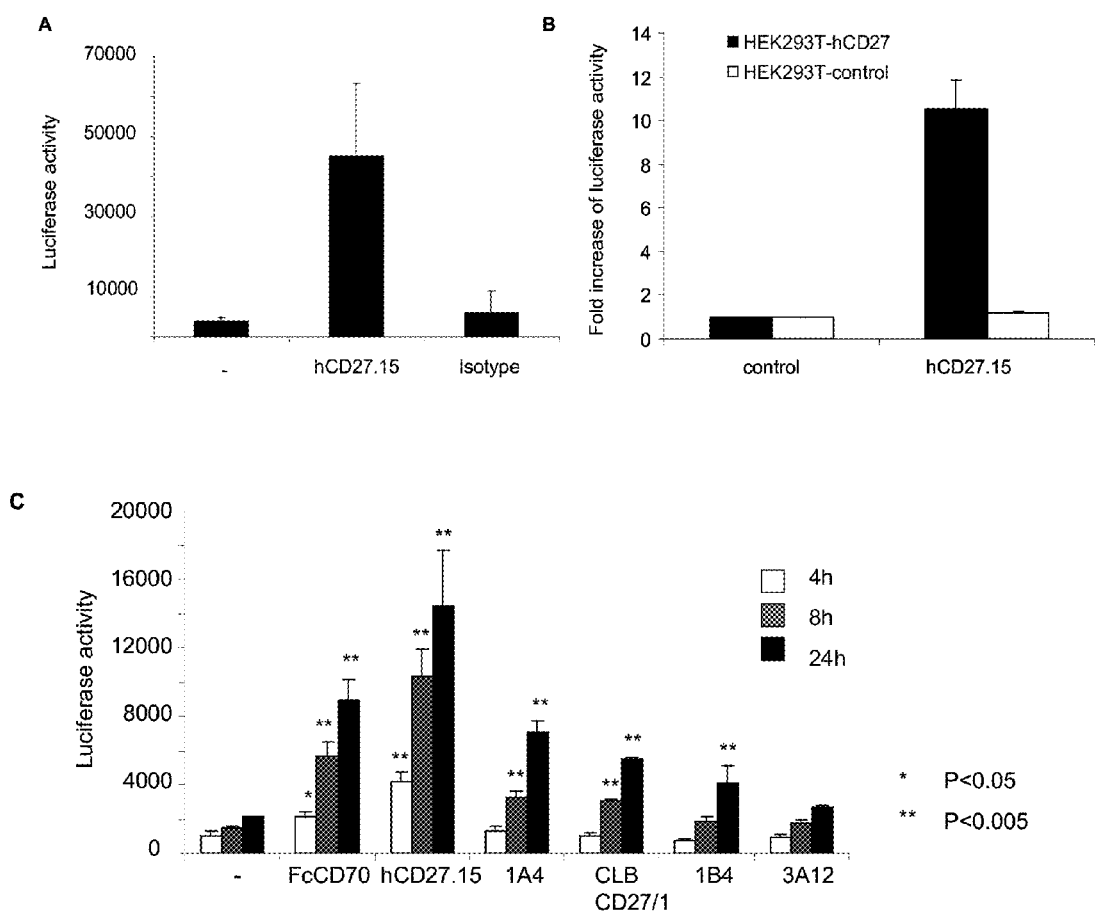
FIG. 2. hCD27.15 induces CD27 signaling leading to NF-κB activation. Human embryonic kidney cells (HEK293T) were transiently transfected to express an NF-κB-luciferase reporter construct together with a hCD27 encoding vector or a control vector. The cells were stimulated for 20 hours in presence or absence of hCD27.15 mAb (10 μg/ml). Stimulation with hCD27.15 mAb revealed specific CD27-induced NF-κB activation, as read out by luciferase activity. (A) Absolute values of luciferase activity as read out by luciferin bioluminescence after stimulation of hCD27-expressing HEK293T cells with mAb hCD27.15 or an isotype control mAb. Data represent triplicate measurements from 1 experiment (+SD). Significance was measured using 2-tailed Student's t test. (B) Fold induction of luciferase activity after stimulation of HEK293T cells transfected to express hCD27 or control vector with hCD27.15 mAb. Data were obtained from 3 independent experiments (N=3+SD). (C) hCD27.15 is superior to other hCD27 agonists. HEK293T cells expressing CD27 and the NF-κB-luciferase reporter were stimulated with soluble agonistic recombinant CD70 protein (Fc-mCD70, 2 μg/ml), mAb hCD27.15 (10 μg/ml), or equal concentrations of other mAbs directed against hCD27. Luciferase activity was read out at the indicated time points. Data represent triplicate measurements from 1 experiment (+SD). Significance was measured using 2-tailed Student's t test.

Functional Profiling of Mouse Anti-Human CD27 Antibodies hCD27.15 Induces CD27 Signaling Leading to NF-KB Activation The full length human CD27 cDNA was cloned into the pcDNA3 expression vector and transiently expressed by transfection into HEK293T human embryonic kidney cells (HEK293T), using FuGENE6 transfection reagent (Roche). CD27 expression from this construct was validated by flow cytometry. To read out hCD27 signaling in response to binding of hCD27.15 mAb, HEK293 cells were transiently co-transfected with the hCD27 pcDNA vector or empty control vector and an NF-κB-luciferase reporter construct, encoding the luciferase gene driven by a minimal NF-κB-responsive promoter (Bonehill et al., 2008, Mol Ther 16(6): 1170-80). At 20 h after transfection, the cells were stimulated for 4, 8, 20 or 24 hours in presence or absence of hCD27.15 mAb (10 µg/ml), other CD27 antibodies (described in Table 2, 10 µg/ml) or FcCD70 (2 µg/ml). After stimulation, cells were washed with ice cold PBS and lysed with Cell Culture Lysis buffer (Promega, Luciferase assay system, catalog number E1500). Luciferase activity was measured after substrate was added to cell lysates following protocol of manufacturer (Luminometer Centro XS3 LB 960, Berthold Technologies). Data was analysed using Mikrowin 2000 software. FIG. 2 illustrates that hCD27.15 activating CD27 more potently than other hCD27 antibodies and FcCD70.

hCD27.15 Costimulates Human CD4$^+$ CD25$^-$ T Cells

Figure 3:
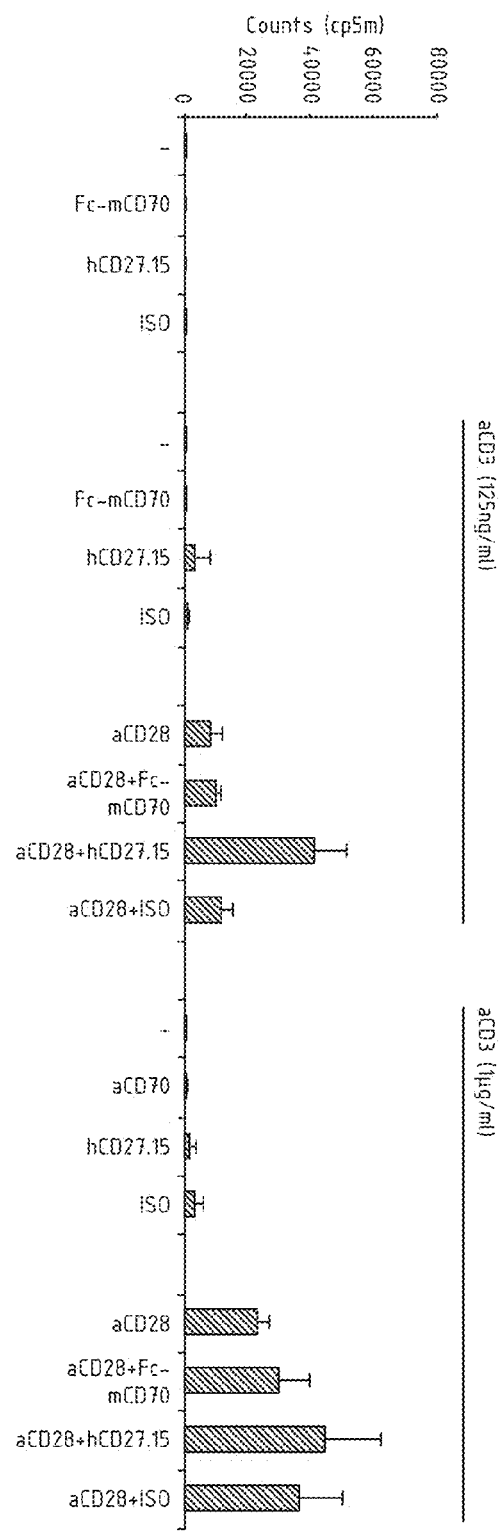
FIG. 3. hCD27.15 induces proliferation and/or promotes survival of $CD^+$ $CD25^-$ T-cells. $CD^+$ $CD25^-$ T-cells were isolated by MACS (neg. selection) from human PBMC's and cultured in 96 well-plates at a concentration of $1 \times 10^5$ cells/well. Stimuli were added as indicated in the Figure and proliferation was determined by [$^3$H] thymidine incorporation.

The effect of activating CD27 with the hCD27.15 antibody on naïve human CD4$^+$CD25$^-$ T cells was determined as follows. PBMCs were isolated from Buffy coat using Ficoll gradient centrifugation according to the manufacturer's instruction (Ficoll-Paque™ Plus cat. Number 17-1440-03). Untouched CD4$^+$CD25$^-$ T-cells were isolated from these PBMC's by MACS based negative selection using the CD4+ T-cell isolation kit II (Miltenyi cat. No 130-091-155) and CD25 microbeads II (Miltenyi cat. No 130-092-983) according to the manufacturer's instructions. Purified CD4+CD25− cells were seeded in 96 well-plates at a concentration of $1\times10^5$ cells/well. Prior to culturing CD4+CD25− cells were checked for purity by flow cytometry. Cells were incubated with different combinations of anti-CD3 (OKT-3), anti-CD28 (1 µg/ml:clone 15E8, Sanquin), Fc-CD70 (2 µg/ml), isotype control (MOPC-21, 10 µg/ml) and hCD27.15 (10 µg/ml), as indicated for FIG. 3. The next day, proliferation was detected by [$^3$H] thymidine incorporation. hCD27.15 stimulated the proliferation of human CD4+CD25− cells under suboptimal stimulation conditions.

hCD27.15 Costimulates Human CD8+ T Cells

The effect of activating CD27 by the hCD27.15 antibody on naïve human CD8+ T cells was examined as follows. PBMCs were isolated from buffy coat using Ficoll gradient centrifugation. Untouched naïve CD8+ T-cells were isolated from these PBMC by MACS-based negative selection using the BD IMag™ human naïve CD8+ T cell enrichment kit (BD cat number 558569), according to the manufacturer's instructions. The CD8+ T cells selected were checked for purity and naïvety by flow cytometry using anti-CD8 and anti-CD45RA antibodies and were labeled with carboxyfluorescein succinimidyl ester (CFSE, 5 µm) according to manufacturer's protocol (Invitrogen). Next, they were seeded in 96 well-plates at a concentration of $1.0\times10^5$ cells/well. Cells were stimulated with soluble anti-CD3 mAb CLB-T3/4E (Pelicluster) at 10 µg/ml (used s/n of hybridoma culture), anti-CD28 mAb CLB-CD28/1 (Pelicluster) at 0.02 µg/ml, in presence of hCD27.15 at 10 µg/ml or isotype control.

Figure 4:
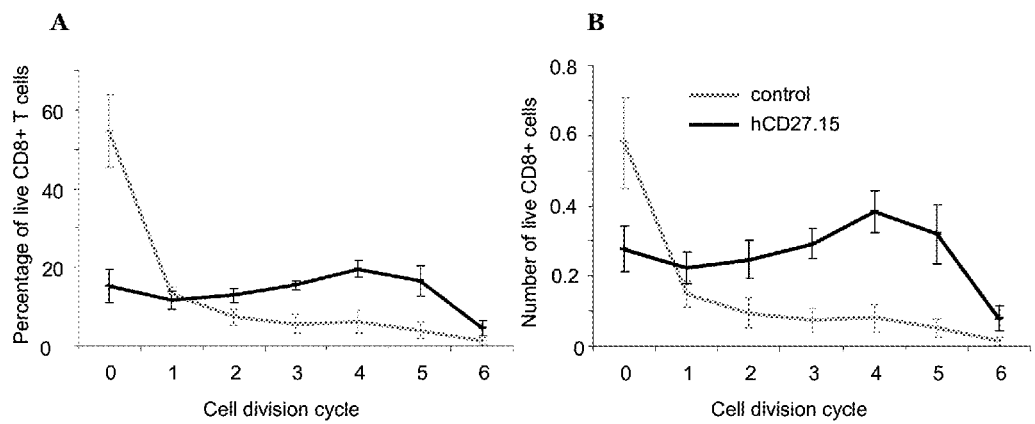
FIG. 4A-B. hCD27.15 induces proliferation and/or promotes survival of naïve $CD8^+$ T-cells. Naïve $CD8^+$ T cells were purified from human PBMC, labeled with CFSE and stimulated for 6 days with anti-CD3 and anti-CD28 mAbs in presence or absence of hCD27.15 mAb (10 μg/ml). hCD27.15 mAb stimulates cell division, as hallmarked by the percentage of cells in each division cycle (A) and total live cell yield, as hallmarked by the absolute number of cells in each division cycle (B). Data were obtained from 4 independent experiments with cells of 4 healthy individuals (N=4+/−SEM).

After culture for the indicated number of days, cells were counted using a CASY cell counter (Scharfe System GmbH), viability was determined by using propidium iodide (PI) and the number of cell divisions the T cells had undergone was assessed by flow cytometric analysis of CFSE fluorescence intensity (FACS Calibur). FIG. 4 illustrates that hCD27.15 is also promoting survival and proliferation of CD8+ cells.

hCD27.15 Stimulates CD8+ T Cells to Produce Specific Cytokines

Figure 5:
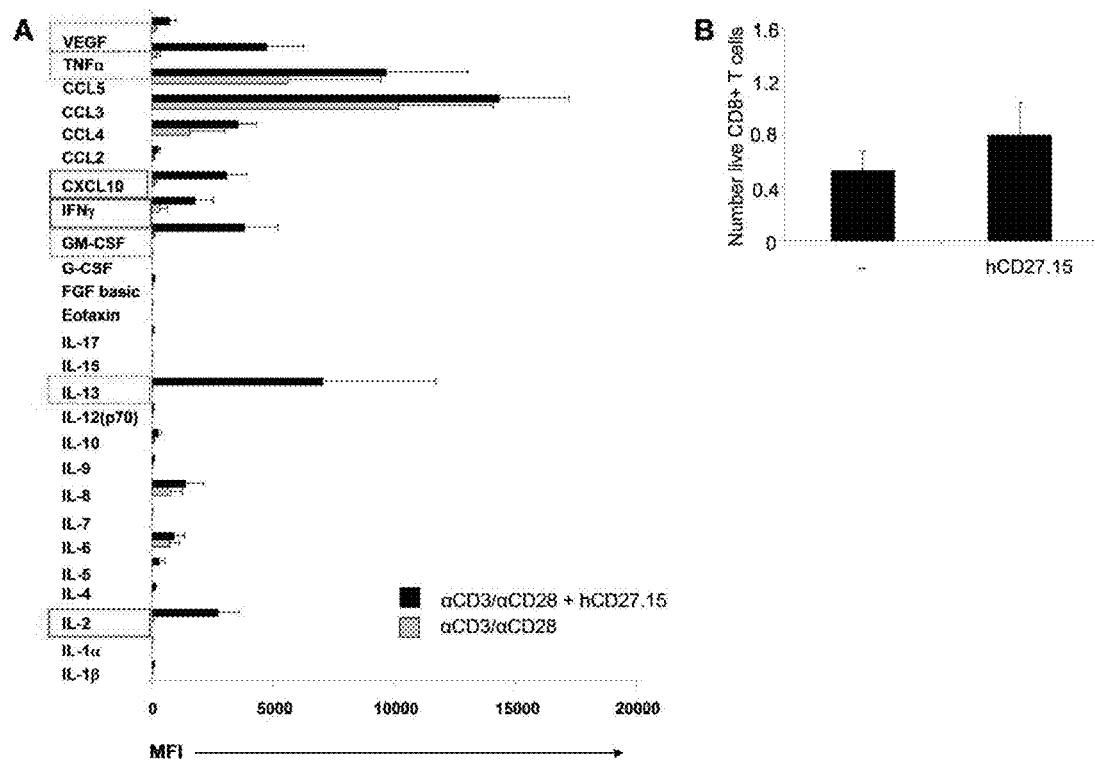
FIG. 5. hCD27.15 stimulates $CD8^+$ T cells to produce specific cytokines Naïve CDS+ T cells were isolated as indicated for FIG. 3 and stimulated with anti-CD3 and anti-CD28 mAb in presence or absence of hCD27.15 mAb (10 μg/ml). (A) After culture for 72 hours, supernatants of cells were taken and cytokines were measured by using Luminex assay. (B) Cell numbers were not significantly different after 72 hours of culture, indicating a qualitative difference in the secretion of certain cytokines (A,B) Data obtained from 3 independent experiments with cells of 3 healthy individuals (N=3+/−SEM).

Human naïve CD8+ T cells were purified and stimulated as indicated above. Culture supernatants were taken after 72 h of culture and analyzed for cytokine secretion by 27-Plex Luminex according to manufacturer's instructions (Biorad, cat. no. 171A11127). As shown in FIG. 5A, hCD27.15 induced the secretion of TNF-α, IL-2, IFN-γ, CXCL10, IL-13 and GM-CSF. In addition, cells were used to perform intracellular staining for IL-2 and IFNγ. After 72 hours of culture, cells were cultured with PMA (conc) and ionomycin (conc) for 4 hours in the presence of Golgi-Plug (1 µg/ml: BD Biosciences). The total number of CD8+ cells is not dramatically different between hCD27.15 and none stimulated cells indicating that the increased secretion of cytokines is merely caused by a qualitative increase of cytokines per cell (FIG. 5B).

Example 4 hCD27.15 Antibody Sequences

Cloning of Immunoglobulin cDNAs

Degenerate primer PCR-based methods were used to determine the DNA sequences encoding the variable regions for the mouse antibody that is expressed by hybridoma hCD27.15. Total RNA was isolated from $5\times10^6$ hybridoma cells using TRIZOL (Invitrogen), and gene specific cDNAs for the heavy and light chains were synthesized using the M-MLV Reverse Transcriptase, RNase H Minus, point mutant kit (Promega, cat. no. M368C) according to the manufacturer's instructions. The $V_H$ and $V_L$ genes were PCR-amplified using a Novagen-based Ig-primer set (Novagen, San Diego, Calif.) and Taq polymerase (Invitrogen). All PCR products that matched the expected amplicon size of 500 bp were cloned into pCR4 TOPO vector (Invitrogen), and the constructs were transformed in One Shot Competent Top10 E. coli (Invitrogen) according to the manufacturer's instructions.

Clones were screened by colony PCR using universal M13 forward and reverse primers, and at least two clones from each reaction were selected for DNA sequencing analysis. CDRs were identified following the Kabat rules (Kabat et al., 1991. Sequences of Proteins of Immunological Interest, Fifth Edition, NIH Publication No. 91-3242). The amino acid sequences were confirmed by mass spectrometry.

The sequences are disclosed in the attached Sequence Listing, FIG. 6 and listed in Table 4.

TABLE 4

Sequence ID numbers for murine anti-human hCD27.15 antibody of this invention.

| SEQ ID NO: | Description |
| --- | --- |
| 1 | hCD27.15 heavy chain variable region (DNA) |
| 2 | hCD27.15 light chain variable region (DNA) |
| 3 | hCD27.15 heavy chain variable region (AA) |
| 4 | hCD27.15 light chain variable region (AA) |
| 5 | hCD27.15 heavy chain CDR1 (AA) |
| 6 | hCD27.15 heavy chain CDR2 (AA) |
| 7 | hCD27.15 heavy chain CDR3 (AA) |
| 8 | hCD27.15 light chain CDR1 (AA) |
| 9 | hCD27.15 light chain CDR2 (AA) |
| 10 | hCD27.15 light chain CDR3 (AA) |

The invention is further described by the following numbered paragraphs:

1. A binding compound, which binds the same epitope of human CD27 as monoclonal antibody hCD27.15, produced by hybridoma hCD27.15 which was deposited with the ATCC in on Jun. 2, 2010 under number PTA-11008.

2. The binding compound of paragraph 1, comprising:
   an antibody heavy chain variable region comprising at least one CDR selected from the group consisting of SEQ ID NOs: 5, 6 and 7, or a variant of any of said sequences; and/or
   an antibody light chain variable region comprising at least one CDR selected from the group consisting of SEQ ID NOs: 8, 9 and 10, or a variant of any of said sequences.

3. The binding compound of paragraph 1 or 2, comprising:
   a heavy chain variable region comprising the amino acid sequence of SEQ ID NO: 3 and a light chain variable region comprising the amino acid sequence of SEQ ID NO: 4.

4. The binding compound of paragraph 1 or 2, which binds to CD27 and comprises:
   an antibody heavy chain variable region comprising the CDRs of SEQ ID NOs: 5, 6 and 7, or a variant of any of said sequences; and/or
   an antibody light chain variable region comprising the CDRs of SEQ ID NOs: 8, 9 and 10, or a variant of any of said sequences.

5. The binding compound of any one of the paragraphs 1-4, wherein any of said variant(s) comprise up to three amino acid modifications.

6. The binding compound of any one of the paragraphs 1-5, which compound is monoclonal antibody hCD27.15 as produced by hybridoma hCD27.15 (deposit accession number PTA-11008) or a humanized version thereof.

7. The binding compound of any of the preceding paragraphs, wherein the binding compound:
    binds human CD27 with a $K_D$ of about 100 nM or lower; and
    blocks binding of human CD27 to human CD70 with an $IC_{50}$ of about 10 nM or lower.

8. A binding compound which competes for a binding epitope on human CD27 with any of the binding compounds of paragraphs 1-7, and has one or more of the following characteristics:
    binds human CD27 with a $K_D$ of about 100 nM or lower;
    binds to human CD27 with about the same $K_D$ as an antibody having a heavy chain comprising the amino acid sequence of SEQ ID NO: 3 and a light chain comprising the amino acid sequence of SEQ ID NO: 4;
    blocks binding of human human CD27 to human CD70 with an $IC_{50}$ of about 10 nM or lower.

9. The binding compound of any one of the paragraphs 1-8, which is
    a chimeric antibody or a fragment thereof;
    a human antibody or a fragment thereof;
    a humanized antibody or a fragment thereof; or
    an antibody fragment selected from the group consisting of Fab, Fab', Fab'-SH, Fv, scFv, F(ab')$_2$, bispecific mAb and a diabody.

10. An isolated polynucleotide encoding the binding compound of any one of the paragraphs 1-9.

11. Isolated polynucleotide of paragraph 10, comprising SEQ ID NOs 1 and 2, which encode the heavy and light chain of hCD27.15.

12. Expression vector comprising the polynucleotide of paragraph 10 or 11.

13. Host cell comprising the expression vector of paragraph 11 or the polynucleotide of paragraph 10 or 11.

14. A method of producing a binding compound of any one of the paragraphs 1-9, which method comprises:
    a) culturing host cell comprising an expression vector that comprises a polynucleotide encoding a binding compound of the invention under the control of suitable regulatory sequences in culture medium under conditions wherein the polynucleotide is expressed, thereby producing polypeptides comprising the light and heavy chain variable regions; and
    b) recovering the polypeptides from the host cell or culture medium.

15. Composition comprising a binding compound of any one of the paragraphs 1-9 in combination with a pharmaceutically acceptable carrier or diluent.

16. Composition of paragraph 15, further comprising another active compound, in particular a therapeutically active compound, more in particular an anti-cancer drug.

17. A binding compound of any one of the paragraphs 1-9 for use in therapy and diagnosis.

18. The binding compound of paragraph 17, wherein the therapy comprises
    stimulation of proliferation and/or survival of CD27$^+$ cells;
    treatment of cancer; or
    treatment of an autoimmune disease.

19. A binding compound of any one of the paragraphs 1-9 for use in flow-cytometry, Western blotting, enzyme-linked immunosorbent assay (ELISA) and immunohistochemistry.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. An antibody or antigen-binding fragment thereof, which binds to human CD27 comprising:
   an antibody heavy chain variable region comprising the CDRs of SEQ ID NOs: 5, 6 and 7; and
   an antibody light chain variable region comprising the CDRs of SEQ ID NOs: 8, 9 and 10.

2. The antibody or antigen-binding fragment thereof of claim 1, comprising a heavy chain variable region comprising the amino acid sequence of SEQ ID NO: 3 and a light chain variable region comprising the amino acid sequence of SEQ ID NO: 4.

3. The antibody or antigen-binding fragment thereof of claim 1, which is monoclonal antibody hCD27.15 as produced by hybridoma hCD27.15 (deposit accession number PTA-11008).

4. The antibody or antigen-binding fragment thereof of claim 1, which:
   binds human CD27 with a $K_D$ of about 100 nM or lower; and
   blocks binding of human CD27 to human CD70 with an $IC_{50}$ of about 10 nM or lower.

5. A human or humanized antibody or antigen-binding fragment thereof which competes for binding to human CD27 with an antibody or antigen-binding fragment thereof which binds to human CD27, said antibody or antigen-binding fragment thereof comprising:
   an antibody heavy chain variable region comprising the CDRs of SEQ ID NOs: 5, 6 and 7; and an antibody light chain variable region comprising the CDRs of SEQ ID NOs: 8, 9 and 10,
   wherein said human or humanized antibody or antigen-binding fragment thereof is able to activate human CD27 (hCD27) signaling more effectively than soluble human CD70 fused to the C-terminus of the dimerization domain of IgG1 as measured by NFκB activation in an in vitro assay, wherein said human or humanized antibody is present at a concentration of 10 μg/mL, or wherein said antigen-binding fragment is present at a molar concentration equivalent to 10 μg/mL of said human or humanized antibody, wherein said soluble human CD70 fused to the C-terminus of the dimerization domain of IgG1 is present at a concentration of 2 μg/mL, and wherein hCD27 is expressed in HEK293 cells transient transfected with a hCD27 encoding nucleic acid.

6. The antibody or antigen-binding fragment thereof of claim 1, which is
   a chimeric antibody or an antigen-binding fragment thereof; or
   an antibody fragment selected from the group consisting of Fab, Fab', Fab'-SH, Fv, scFv, F(ab')$_2$, bispecific mAb and a diabody.

7. A polynucleotide encoding the antibody or antigen-binding fragment thereof as claimed in claim 1.

8. The polynucleotide of claim 7, comprising SEQ ID NOs 1 and 2, which encode the heavy and light chain of hCD27.15.

9. An expression vector comprising the polynucleotide of claim 7 or 8.

10. A host cell comprising the expression vector of claim 9.

11. A host cell comprising the polynucleotide of claim 7 or 8.

12. A method of producing an antibody or antigen-binding fragment thereof, which method comprises:
    a) culturing a host cell comprising an expression vector that comprises a polynucleotide encoding the antibody or antigen-binding fragment thereof of claim 1 under the control of suitable regulatory sequences in culture medium under conditions wherein the polynucleotide is expressed, thereby producing polypeptides comprising the light and heavy chain variable regions; and
    b) recovering the polypeptides from the host cell or culture medium.

13. A composition comprising the antibody or antigen-binding fragment thereof of claim 1 in combination with a pharmaceutically acceptable carrier or diluent.

14. The composition of claim 13, further comprising an anti-cancer drug.

15. The antibody or antigen-binding fragment thereof of claim 1, wherein said antibody or antigen-binding fragment thereof exhibits agonist activity on CD27.

16. The antibody or antigen-binding fragment thereof of claim 1, wherein said antibody or antigen-binding fragment thereof is able to activate human CD27 (hCD27) signaling more effectively than soluble human CD70 fused to the C-terminus of the dimerization domain of IgG1 as measured by NFκB activation in an in vitro assay, wherein said antibody is present at a concentration of 10 μg/mL, or wherein said antigen-binding fragment is present at a molar concentration equivalent to 10 μg/mL of said antibody, wherein said soluble human CD70 fused to the C-terminus of the dimerization domain of IgG1 is present at a concentration of 2 μg/mL, and wherein hCD27 is expressed in HEK293 cells transient transfected with a hCD27 encoding nucleic acid.

17. The antibody or antigen-binding fragment thereof of claim 1, wherein said antibody or antigen-binding fragment thereof binds human CD27 with at least a $K_D$ of $10^{-6}$M.

18. The antibody or antigen binding fragment thereof of claim 5, which has one or more of the following characteristics:
    binds human CD27 with a $K_D$ of about 100 nM or lower;
    binds to human CD27 with about the same $K_D$ as an antibody having a heavy chain comprising the amino acid sequence of SEQ ID NO: 3 and a light chain comprising the amino acid sequence of SEQ ID NO: 4; and/or
    blocks binding of human CD27 to human CD70 with an $IC_{50}$ of about 10 nM or lower.

19. A human or humanized version of the antibody or antigen-binding fragment thereof of claim 1.

* * * * *

SEQUENCE LISTING

```
<160> NUMBER OF SEQ ID NOS: 10

<210> SEQ ID NO 1
<211> LENGTH: 396
<212> TYPE: DNA
<213> ORGANISM: Mus musculus

<400> SEQUENCE: 1
tcagaggttc ggctgcagca gtctggggca gaccttgtga agccaggggc ctcagtcaag      60
ttgtcctgca cagcttctgg cttcatcatt aaagccacct atatgcactg ggtgaggcag     120
aggcctgaac agggcctgga gtggattgga aggattgatc ctgcgaatgg tgagactaaa     180
tatgacccga agttccaggt caaggccact ataacagcag acacatcctc cagcacagcc     240
tacctgcagc tcaacagcct gacatctgac gacactgccg tctattactg tgctagatac     300
gcctggtact tcgatgtctg gggcgcaggg accacggtca ccgtctcctc agccaaaacg     360
acacccccay ccgtttatcc mytggyccct ggaagc                               396

<210> SEQ ID NO 2
<211> LENGTH: 381
<212> TYPE: DNA
<213> ORGANISM: Mus musculus

<400> SEQUENCE: 2
```

```
gacatccaga tgactcagtc tccagcctcc ctgtctgcat ctgtgggaga cactgtcact      60
atcacatgtc gggcaagtga aaatatttac agttttttag catggtatca tcagaaacag     120
ggaaggtctc cgcaactcct ggtctatcat gcaaaaaccc tagcagaagg tgtgccatca     180
aggttcagtg gcagtggatc aggcacacag tttttctctga agatcaacag cctgcaggct    240
gaagattttg ggagttatta ctgtcaacat tattatggta gtccgctcac gttcggtgct     300
gggaccaagc tggaggtgaa acgggctgat gctgcaccaa ctgtatccat cttyccrccc     360
tcctcwgagg agctaagctt g                                               381
```

```
<210> SEQ ID NO 3
<211> LENGTH: 131
<212> TYPE: PRT
<213> ORGANISM: Mus musculus
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 3
```

Glu Val Arg Leu Gln Gln Ser Gly Ala Asp Leu Val Lys Pro Gly Ala
1               5                   10                  15

Ser Val Lys Leu Ser Cys Thr Ala Ser Gly Phe Ile Ile Lys Ala Thr
            20                  25                  30

Tyr Met His Trp Val Arg Gln Arg Pro Glu Gln Gly Leu Glu Trp Ile
        35                  40                  45

Gly Arg Ile Asp Pro Ala Asn Gly Glu Thr Lys Tyr Asp Pro Lys Phe
    50                  55                  60

Gln Val Lys Ala Thr Ile Thr Ala Asp Thr Ser Ser Thr Ala Tyr
65                  70                  75                  80

Leu Gln Leu Asn Ser Leu Thr Ser Asp Asp Thr Ala Val Tyr Tyr Cys
                85                  90                  95

Ala Arg Tyr Ala Trp Tyr Phe Asp Val Trp Gly Ala Gly Thr Thr Val
            100                 105                 110

Thr Val Ser Ser Ala Lys Thr Thr Pro Pro Xaa Val Tyr Pro Xaa Xaa
        115                 120                 125

Pro Gly Ser
    130

```
<210> SEQ ID NO 4
<211> LENGTH: 127
<212> TYPE: PRT
<213> ORGANISM: Mus musculus

<400> SEQUENCE: 4
```

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Phe
            20                  25                  30

Leu Ala Trp Tyr His Gln Lys Gln Gly Arg Ser Pro Gln Leu Leu Val
        35                  40                  45

Tyr His Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ala
65                  70                  75                  80

Glu Asp Phe Gly Ser Tyr Tyr Cys Gln His Tyr Tyr Gly Ser Pro Leu
                85                  90                  95

Thr Phe Gly Ala Gly Thr Lys Leu Glu Val Lys Arg Ala Asp Ala Ala
            100                 105                 110

Pro Thr Val Ser Ile Phe Pro Pro Ser Ser Glu Glu Leu Ser Leu
        115                 120                 125

<210> SEQ ID NO 5
<211> LENGTH: 10
<212> TYPE: PRT
<213> ORGANISM: Mus musculus

<400> SEQUENCE: 5

Gly Phe Ile Ile Lys Ala Thr Tyr Met His
1               5                   10

<210> SEQ ID NO 6
<211> LENGTH: 17
<212> TYPE: PRT
<213> ORGANISM: Mus musculus

<400> SEQUENCE: 6

Arg Ile Asp Pro Ala Asn Gly Glu Thr Lys Tyr Asp Pro Lys Phe Gln
1               5                   10                  15

Val

<210> SEQ ID NO 7
<211> LENGTH: 7
<212> TYPE: PRT
<213> ORGANISM: Mus musculus

<400> SEQUENCE: 7

Tyr Ala Trp Tyr Phe Asp Val
1               5

<210> SEQ ID NO 8
<211> LENGTH: 11
<212> TYPE: PRT
<213> ORGANISM: Mus musculus

<400> SEQUENCE: 8

Arg Ala Ser Glu Asn Ile Tyr Ser Phe Leu Ala
1               5                   10

<210> SEQ ID NO 9
<211> LENGTH: 7
<212> TYPE: PRT
<213> ORGANISM: Mus musculus

<400> SEQUENCE: 9

His Ala Lys Thr Leu Ala Glu
1               5

<210> SEQ ID NO 10
<211> LENGTH: 9
<212> TYPE: PRT
<213> ORGANISM: Mus musculus

<400> SEQUENCE: 10

Gln His Tyr Tyr Gly Ser Pro Leu Thr
1               5